United States Patent
Dorsett, Jr.

(10) Patent No.: US 7,085,773 B2
(45) Date of Patent: *Aug. 1, 2006

(54) LABORATORY DATABASE SYSTEM AND METHODS FOR COMBINATORIAL MATERIALS RESEARCH

(75) Inventor: David R. Dorsett, Jr., Slidell, LA (US)

(73) Assignee: Symyx Technologies, Inc., Santa Clara, CA (US)

( * ) Notice: Subject to any disclaimer, the term of this patent is extended or adjusted under 35 U.S.C. 154(b) by 142 days.

This patent is subject to a terminal disclaimer.

(21) Appl. No.: 10/250,618

(22) PCT Filed: Jan. 7, 2002

(86) PCT No.: PCT/US02/00466

§ 371 (c)(1), (2), (4) Date: Dec. 29, 2003

(87) PCT Pub. No.: WO02/054188

PCT Pub. Date: Jul. 11, 2002

(65) Prior Publication Data

US 2004/0088117 A1 May 6, 2004

Related U.S. Application Data

(63) Continuation-in-part of application No. 09/755,623, filed on Jan. 5, 2001, now Pat. No. 6,658,429.

(51) Int. Cl.
*G06F 17/00* (2006.01)

(52) U.S. Cl. .............................. 707/104; 707/1; 707/100
(58) Field of Classification Search .................. 707/104, 707/1, 100, 103; 382/282; 717/103, 108; 703/17

See application file for complete search history.

(56) References Cited

U.S. PATENT DOCUMENTS 4,862,345 A 8/1989 Lekron ........................ 364/188

(Continued)

FOREIGN PATENT DOCUMENTS

| WO | WO 96/11878 | 4/1996 |
|----|-------------|--------|
| WO | WO 97/31127 | 8/1997 |
| WO | WO 98/15825 | 4/1998 |
| WO | WO 99/33003 | 7/1999 |
| WO | WO 01/65415 | 9/2001 |
| WO | WO 03/005249 | 1/2003 |

OTHER PUBLICATIONS

Kagaku, "Combinatorial Chemistry: Inconceivable without Computers", *Combinatorial Chemistry*, vol. 51, No. 8, pp. 480–483 & 583 (1996). Original Japanese reference and English translation included.

(Continued)

*Primary Examiner*—Sanjiv Shah

(57) ABSTRACT

Systems, methods, and apparatus, including computer program apparatus, are described for implementing techniques for processing data from a combinatorial experiment. The techniques include receiving data from a chemical experiment on a library of materials having a plurality of members and generating a representation of the chemical experiment. The representation includes data defining an experiment object having a plurality of properties derived from the chemical experiment. The experiment object is associated with the library of materials. The representation also includes data defining one more element objects. Each element object is associated with one or more members of the library of materials. A data model and corresponding data structures for describing such experiments are also disclosed.

32 Claims, 18 Drawing Sheets

U.S. PATENT DOCUMENTS

| | | | |
|---|---|---|---|
| 4,965,743 A | 10/1990 | Malin et al. | 364/513 |
| 5,008,810 A | 4/1991 | Kessel et al. | 364/200 |
| 5,392,209 A | 2/1995 | Eason et al. | 364/413.01 |
| 5,398,336 A | 3/1995 | Tantry et al. | 395/600 |
| 5,434,971 A | 7/1995 | Lysakowski, Jr. | 395/200 |
| 5,446,575 A | 8/1995 | Lysakowski, Jr. | 395/200.01 |
| 5,446,842 A | 8/1995 | Schaeffer et al. | 935/200.01 |
| 5,463,564 A | 10/1995 | Agrafiotis et al. | 364/496 |
| 5,511,186 A | 4/1996 | Carhart et al. | 395/600 |
| 5,544,297 A | 8/1996 | Milne et al. | 395/154 |
| 5,574,656 A | 11/1996 | Agrafiotis et al. | 364/500 |
| 5,604,892 A | 2/1997 | Nuttall et al. | 395/500 |
| 5,623,592 A | 4/1997 | Carlson et al. | 395/348 |
| 5,634,129 A | 5/1997 | Dickinson | 395/683 |
| 5,717,877 A | 2/1998 | Orton et al. | 395/326 |
| 5,764,897 A | 6/1998 | Khalidi | 395/200.31 |
| 5,768,505 A | 6/1998 | Gilchrist et al. | 395/200.31 |
| 5,778,378 A | 7/1998 | Rubin | 707/103 |
| 5,781,732 A | 7/1998 | Adams | 395/200.35 |
| 5,787,283 A | 7/1998 | Chin et al. | 395/701 |
| 5,787,425 A | 7/1998 | Bigus | 707/6 |
| 5,794,001 A | 8/1998 | Malone et al. | 395/342 |
| 5,862,514 A | 1/1999 | Huse et al. | 702/22 |
| 5,878,432 A | 3/1999 | Misheski et al. | 707/103 |
| 5,920,871 A | 7/1999 | Macri et al. | 707/104 |
| 5,936,860 A | 8/1999 | Arnold et al. | 364/468.01 |
| 5,978,804 A | 11/1999 | Dietzman | 707/10 |
| 6,031,625 A | 2/2000 | Sherman et al. | 358/1.18 |
| 6,044,212 A | 3/2000 | Flavin et al. | 395/500.27 |
| 6,083,276 A | 7/2000 | Davidson et al. | 717/1 |
| 6,125,383 A | 9/2000 | Glynias et al. | 709/202 |
| 6,175,816 B1 | 1/2001 | Flavin et al. | 703/13 |
| 6,185,561 B1 | 2/2001 | Balaban et al. | 707/6 |
| 6,189,013 B1 | 2/2001 | Maslyn et al. | 707/6 |
| 6,266,805 B1 | 7/2001 | Nwana et al. | 717/4 |
| 6,314,555 B1 | 11/2001 | Ndumu et al. | 717/1 |
| 6,363,399 B1 | 3/2002 | Maslyn et al. | 707/104.1 |
| 6,389,380 B1 * | 5/2002 | Bankes | 703/17 |
| 6,408,308 B1 | 6/2002 | Maslyn et al. | 707/104.1 |
| 6,411,945 B1 | 6/2002 | Nakajima | 706/19 |
| 6,453,333 B1 | 9/2002 | Glynias et al. | 709/202 |
| 6,507,945 B1 * | 1/2003 | Rust et al. | 717/103 |
| 6,519,611 B1 | 2/2003 | Zong | 707/104.1 |
| 6,581,020 B1 | 6/2003 | Buote et al. | 702/123 |
| 6,584,412 B1 | 6/2003 | Brecher | 702/27 |
| 6,594,588 B1 | 7/2003 | Peden et al. | 702/32 |
| 6,618,852 B1 * | 9/2003 | van Eikeren et al. | 717/108 |
| 6,647,342 B1 | 11/2003 | Iglesia et al. | 702/22 |
| 6,658,429 B1 * | 12/2003 | Dorsett, Jr. | 707/1 |
| 6,681,198 B1 | 1/2004 | Buote et al. | 702/185 |
| 6,718,336 B1 | 4/2004 | Saffer et al. | 707/102 |
| 6,738,529 B1 * | 5/2004 | Crevier et al. | 382/282 |
| 6,862,533 B1 | 3/2005 | Strehlau et al. | 702/22 |
| 2001/0047398 A1 | 11/2001 | Rubenstein | 709/218 |
| 2003/0055849 A1 | 3/2003 | Thure et al. | 707/500 |

OTHER PUBLICATIONS

Yamagata et al., "Constructing an Assay System with HTS", *IV High Throughput Screening*, pp. 179–191 (1997). Original Japanese reference and English translation included.

Peggy Harrod, PCT International Search Report, Dec. 3, 2002, Washington, D.C.

Ann M. Thayer, *"Bioinformatics for the Masses"*, Mar. 22, 2000, <http://pubs.acs.org/hotartcl/cenear/000207/7806bus1.html>.

Afferent Systems, Inc., "Afferent Analytical™", pp. 1 of 1, http://www/afferent.com/analytical.html, Copyright© 1996–1999, Last updated Jan. 28, 1999.

Afferent Systems, Inc., "What's New?, IRORI and Afferent enter into Combinatorial Chemistry Collaboration Agreement," pp. 1 of 2, http://www.afferent.com/news.html, Copyright© 1996–1999, Last updated Jul. 3, 1999.

John F. Cargill et al., "Automated Combinatorial Chemistry on Solid Phase," *LRA*, vol. 8, pp. 139–148.

Dimitrie Grigoriadis et al., *APHIL*, "A Relational System For Managing High–Throughput Screening Data," 1997.

Eric W. McFarland et al., *Mat. Tech.*, "Approaches for Rapid Materials Discovery Using Combinatorial Methods," vol. 13, No. 3, 1998, pp. 107–120.

MDL Information Systems, Inc., *MDL Screen User's Guide, Version 1.1*, Dec. 1996.

MDL Information Systems, Inc., *MDL Screen 1.3 Closes Final Gap in HTS Workflow*, pp. 1–8 1998.

*Molecular Connections*, vol. 17, No. 3, Jul. 1998.

*Network Science, Introducing MDL Screen*, http://www-.netsci.org/Science/Screening/feature03.

"Synaptic Smoothes Data Flow Between Chemistry and Biology," *Molecular Connection*, Jul. 1998, pp. 16–18.

Umetri AB, "User's Guide to MODDE, MODDE 4.0, Improve and Optimize Products and Processes," May 15, 1997.

Bayard et al. "Connecting Scientific Programs and Data Using Databases", IEEE Data Engineering Bulletin, vol. 16, 1993, (6 pages).

Berard et al., "Scientific Data Management in the Environmental Molecular Sciences Laboratory", Proc. 14th IEEE Symposium on Mass Storage Systems, 1995 (17 pages).

Chen et al., "An Overview of the Object Protocol Model (OPM) and the OPM Data Management Tools", Information Systems, vol. 20, 1995, pp. 393–418.

Gasteiger et al. "Computer–Assisted Planning of Organic Syntheses: The Second Generation of Programs", Angew. Chem. Int. Ed. Engl. 1995, 34, pp. 2613–2633.

Houstis et al., "The Architecture of a Software Framework for Building Problem Solving Environments for PDE Based Applications", Dept. of Computer Sciences Purdue University, May 14, 1997.

Ioannidis et al., "Conceptual Schemas: Multi–Faceted Tools For Desktop Scientific Experiment Management", Int. J. Cooperative Information Systems, vol. 1, 1992 (24 pages).

Ioannidis et al., "Desktop Experiment Management", IEEE Data Eng. Bull., vol. 16, 1993, pp. 19–23.

Ioannidis et al., "FROG and TURTLE: Visual Bridges Between Files and Object–Oriented Data", Proc. Of the 8th International Conference on Scientific and Statistical Database Management, Stockholm, Sweden, 1996, pp. 76–85.

Ioannidis et al., "ZOO: A Desktop Experiment Management Environment", Proceedings of the 22th VLDB Conference Mumbai(Bombay), India, 1996 (12 pages).

Keller et al., "Metadata: The Foundation of Effective Effective Experiment Management", Proc. Of the 1st IEEE Metedata Conference, Silver Springs, Maryland, USA, 1996 (12 pages).

Kling "First Steps Toward A Common Language For Analytical Data", Analytical Chemistry News & Features, Sep. 1, 1999, pp. 621A–623A.

Maier et al., "Bambi Meets Godzilla: Object Database for Scientific Computing", Proc. Of the 7th International Working conference on Scientific and Statistical Database Management, IEEE Computer Society: Washington D.C., USA, 1994, pp. 176–184.

Medeiros et al., "WASA: A Workflow–Based Architecture to Support Scientific Database Applications", Proc. 6$^{th}$ International Conference on Database and Expert Systems Applications, 1995 (20 pages).

Microsoft Automation and Extensibility Overview, Feb. 2002, download on Aug. 18, 2004 from: http://msdn.microsof.com/library/en–us/dv_vstecha. . . soriAutomationExtensibiltyOverview.asp?frame=true.

Microsoft Building A Custom Project Wizard in Visual Studio.NET, May 2003, downloaded on Aug. 18, 2004 from: http://msdn.micrsof.com/library/en–us/dv¯vstechart/htm/customprojectwiz.asp?frame=true.

Microsoft Creating Components in .NET , Feb. 2002, downloaded on Aug. 18, 2004 from: http://msdn.microsof.com/library/en–us/dpdotnet/html/components.asp?frame=true.

Microsoft Writing Custom Designers for .NET Components, Jun. 2001, downloaded on Aug. 18, 2004 from: http://msdn.microof.com/library/en–us/dndotnet/html/custdsgnr-dotnet.asp?frame=true.

Pirklbauer et al., "Libraries and Tools for Object–Oriented Distributed Automation Software", 1993.

Pirklbauer et al., "Object–Oriented and Conventional Process Automated Systems", 1994.

Pirklbauer et al., "Object–Oriented Process Control Software", Journal of Object–Oriented Programming, May 1994.

Pirklbauer et al., "ProcessTalk: An Object Oriented Framework for Distributed Automation Software", 1992.

Pomberger et al., "The Role of Prototyping in Software Development", 1994.

Ugi et al., "Computer–Assisted Solution of Chemical Problems – The Historical Development and the Present State of the Art of a New Discipline of Chemistry", Angew. Chem. Int. Ed. Engl. 1993, 32, pp. 201–227.

Weinreich et al., "The Communication Facilities of the ProcessTalk Application Framework", OOPSLA 1994 Workshop.

* cited by examiner

FIG._1

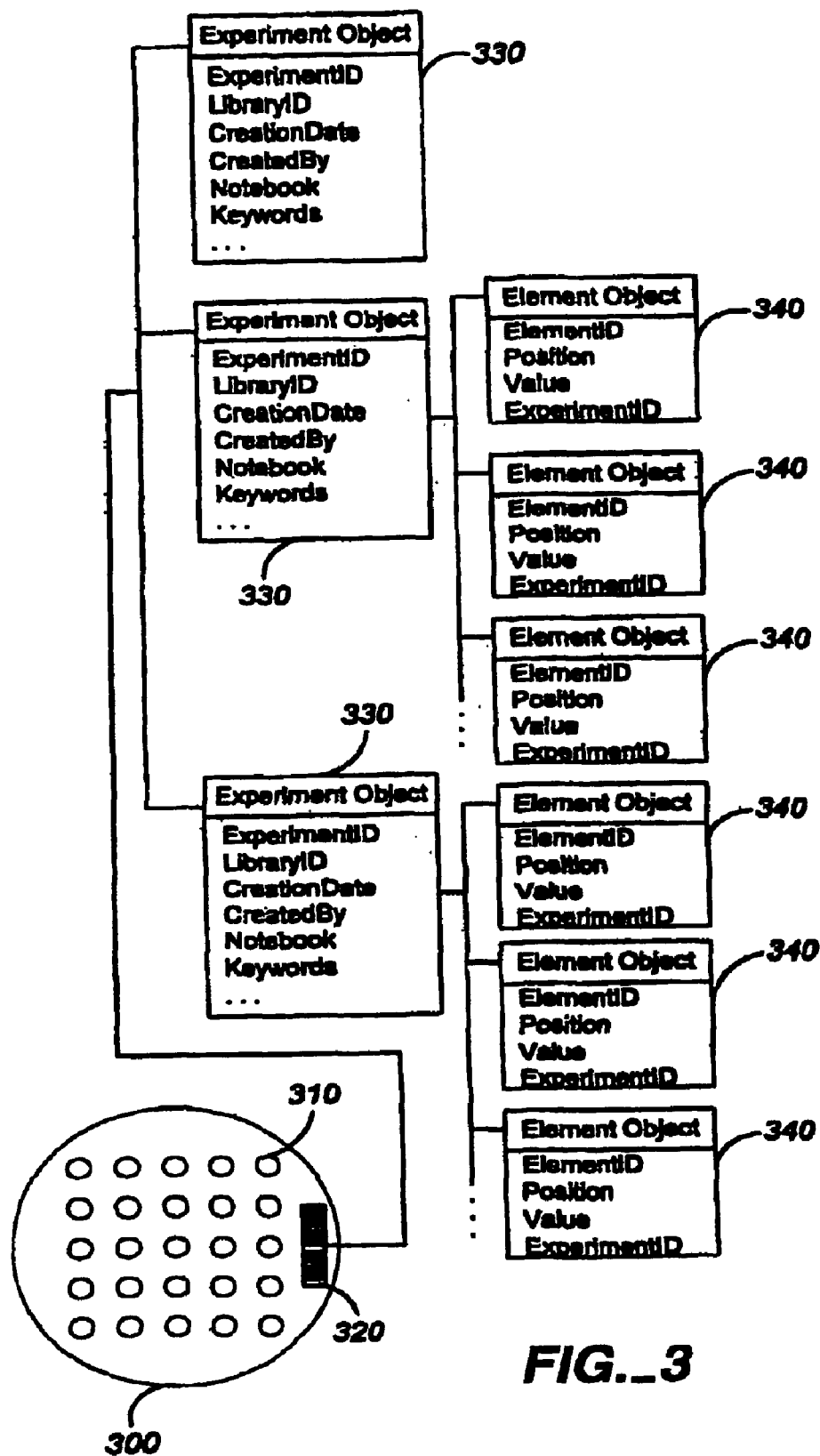
FIG._3

FIG. 4A

| XYDATA | | |
|---|---|---|
| PK | ID | NUMBER(11,0) |
| | CONCHECK | NUMBER(11,0) |
| | CRBY | VARCHAR2(80) |
| | CRDATE | DATE |
| | MODBY | VARCHAR2(80) |
| | MODDATE | DATE |
| | DATA | BLOB |
| | FLAGS | NUMBER(11,0) |
| | TITLE | VARCHAR2(240) |
| | LINE | NUMBER(11,0) |
| | LINECOLOR | NUMBER(11,0) |
| | POINT | NUMBER(11,0) |
| | POINTCOLOR | NUMBER(11,0) |
| | XUNITS | VARCHAR2(80) |
| | XSCALE | NUMBER |
| | XLEGEND | VARCHAR2(240) |
| | YUNITS | VARCHAR2(80) |
| | YSCALE | NUMBER |
| | YLEGEND | VARCHAR2(240) |
| | STATUS | NUMBER(11,0) |
| | XCOLOR | NUMBER(11,0) |
| | YCOLOR | NUMBER(11,0) |
| | MINX | NUMBER |
| | MAXX | NUMBER |
| | MINY | NUMBER |
| | MAXY | NUMBER |
| | PLOTSTYLE | NUMBER(11,0) |
| | XDATASTART | NUMBER |
| | XDATAINTERVAL | NUMBER |
| | YDATA | BLOB |
| | XDATA | BLOB |

*FIG. 4B*

```xml
- <Impressionist_Procedure_1 ID="27" ConCheck="1" PersistState="0">
    <Name>Polymer reaction procedure</Name>
    <Enabled>-1</Enabled>
    <Version>1</Version>
  + <Children>
    <CreationDate>2000/03/27 15:44:26</CreationDate>
    <UserFuncsAndSubs />
    <Computer>DDORSETT</Computer>
  </Impressionist_Procedure_1>
```

*FIG._5A*

| IMPPROCEDURE | | |
|---|---|---|
| PK | ID | NUMBER(11,0) |
| | CONCHECK | NUMBER(11,0) |
| | NAME | VARCHAR2(240) |
| | ENABLED | NUMBER(1,0) |
| | VERSION | NUMBER(11,0) |
| | CHILDREN | CLOB |
| | AUTHOR | VARCHAR2(80) |
| | PROJECT | VARCHAR2(80) |
| | CREATION | DATE |
| | COMMNTS | VARCHAR2(4000) |
| | USERSUBS | CLOB |
| | COMPUTER | VARCHAR2(80) |
| | LOGGINGENABLED | NUMBER(1,0) |

*FIG._5C*

```xml
- <Impressionist_Procedure_1 ID="27" ConCheck="1" PersistState="0">
    <Name>Polymer reaction procedure</Name>
    <Enabled>-1</Enabled>
    <Version>1</Version>
    - <Children>
        - <Impressionist_DefineVariables_1 ID="0" ConCheck="0" PersistState="2" UserID="ddorsett">
            <Name>Define Count Variable</Name>
            <Enabled>-1</Enabled>
            <Version>1</Version>
            <Prompt>No</Prompt>
            <PromptText>Please set the following variables:</PromptText>
            <Definition>Count|1|</Definition>
        </Impressionist_DefineVariables_1>
        - <Impressionist_Container_1 ID="0" ConCheck="0" PersistState="2" UserID="ddorsett">
            <Name>Initialize Arms and Syringes</Name>
            <Enabled>-1</Enabled>
            <Version>1</Version>
            <Comments>This procedure will initialize both arms and the corresponding
                syringes.</Comments>
            - <Children>
                - <Impressionist_InitArm_1 ID="0" ConCheck="0" PersistState="2" UserID="ddorsett">
                    <Name>Initialize Left Arm</Name>
                    <Enabled>-1</Enabled>
                    <Version>1</Version>
                    <Arm>Left Arm</Arm>
                    <Wait>Yes</Wait>
                </Impressionist_InitArm_1>
                - <Impressionist_InitArm_1 ID="0" ConCheck="0" PersistState="2" UserID="ddorsett">
                    <Name>Initialize Right Arm</Name>
                    <Enabled>-1</Enabled>
                    <Version>1</Version>
                    <Arm>Right Arm</Arm>
                    <Wait>Yes</Wait>
                </Impressionist_InitArm_1>
                - <Impressionist_MoveArmSub_1 ID="0" ConCheck="0" PersistState="2" UserID="ddorsett">
                    <Name>Move Left Arm To Waste</Name>
                    <Enabled>-1</Enabled>
                    <Version>1</Version>
                    <Arm>Left Arm</Arm>
                    <Wait>Yes</Wait>
```

*FIG._5B*

```xml
- <Experiment ID="298" ConCheck="1" PersistState="0">
    <CreationDate>2000/05/29 18:44:47</CreationDate>
    <CreatedBy>PPR</CreatedBy>
    <Status>0</Status>
    <ClassName>PPRExperiment</ClassName>
    <Comment />
    <Project>Polyolefins</Project>
    <Notebook>0</Notebook>
    <Flags>0</Flags>
    <Name>DV 1.2 2A</Name>
    <StartDate>2000/05/29 00:00:00</StartDate>
    <LibRows>6</LibRows>
    <LibCols>6</LibCols>
    <Log />
    <LibID>100257</LibID>
  - <Logs>
    + <Log ID="711" ConCheck="1" PersistState="0">
    + <Log ID="712" ConCheck="1" PersistState="0">
    + <Log ID="713" ConCheck="1" PersistState="0">
    + <Log ID="714" ConCheck="1" PersistState="0">
    + <Log ID="715" ConCheck="1" PersistState="0">
    + <Log ID="716" ConCheck="1" PersistState="0">
    + <Log ID="717" ConCheck="1" PersistState="0">
    + <Log ID="718" ConCheck="1" PersistState="0">
    + <Log ID="719" ConCheck="1" PersistState="0">
    + <Log ID="720" ConCheck="1" PersistState="0">
    + <Log ID="721" ConCheck="1" PersistState="0">
    + <Log ID="722" ConCheck="1" PersistState="0">
    + <Log ID="723" ConCheck="1" PersistState="0">
    + <Log ID="724" ConCheck="1" PersistState="0">
    + <Log ID="725" ConCheck="1" PersistState="0">
    + <Log ID="726" ConCheck="1" PersistState="0">
    + <Log ID="727" ConCheck="1" PersistState="0">
    </Logs>
</Experiment>
```

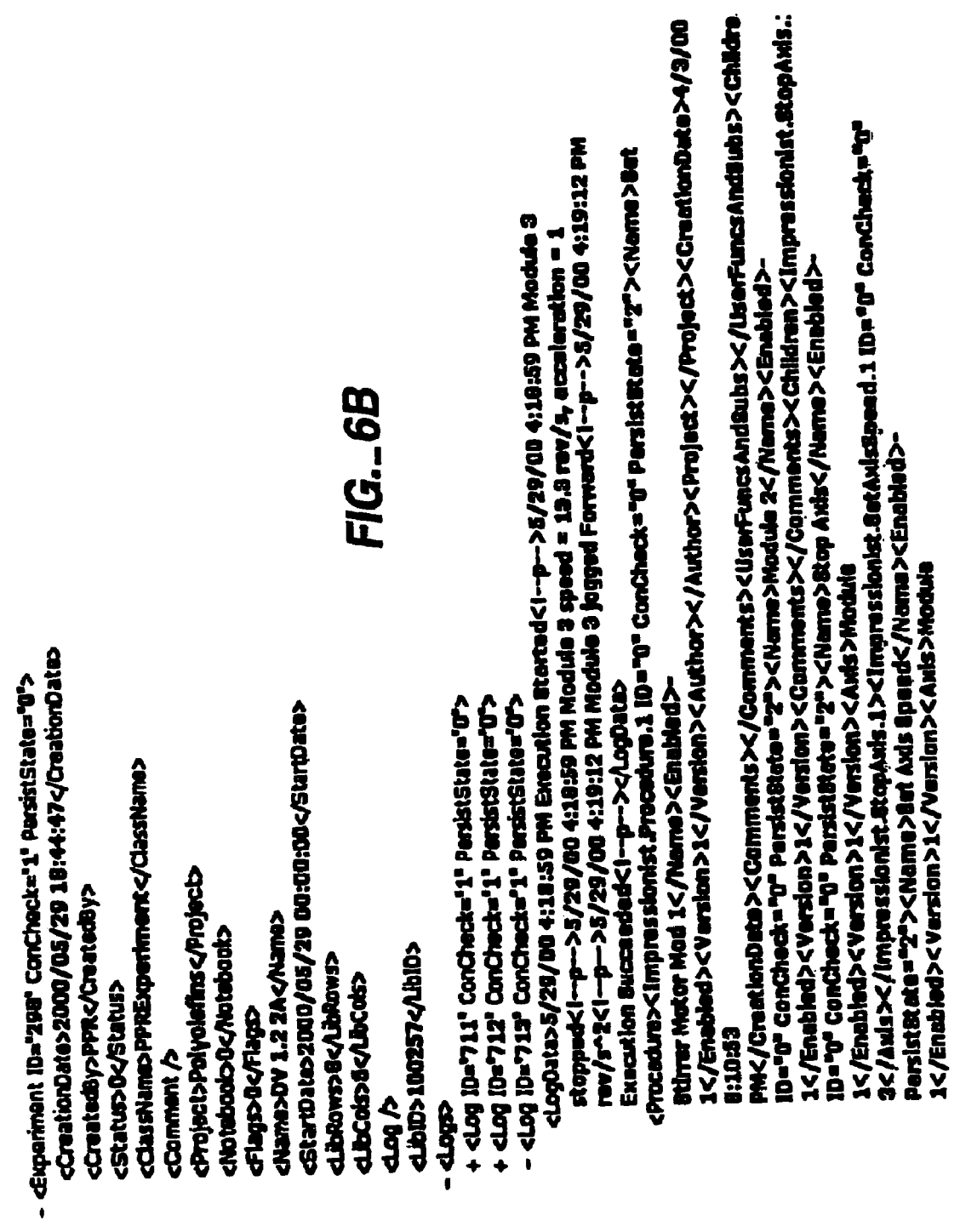

```xml
- <PPRExperiment ID="298" ConCheck="1" PersistState="0">
    <CreationDate>2000/05/29 18:44:47</CreationDate>
    <CreatedBy>PPR</CreatedBy>
    <Status>0</Status>
    <ClassName>PPRExperiment</ClassName>
    <Comment />
    <Project>Polyolefins</Project>
    <Notebook>0</Notebook>
    <Flags>0</Flags>
    <Name>DV 1.2 2A</Name>
    <StartDate>2000/05/29 00:00:00</StartDate>
    <LibRows>8</LibRows>
    <LibCols>6</LibCols>
    <Log />
    <LibID>100257</LibID>
  + <Logs>
  - <PPRElements>
    + <PPRElement ID="3454" ConCheck="1" PersistState="0">
    ⊞ <PPRElement ID="3455" ConCheck="1" PersistState="0">
    - <PPRElement ID="3456" ConCheck="1" PersistState="0">
        <Position>13</Position>
        <Flags>0</Flags>
        <Status>0</Status>
        <PressureID>17016</PressureID>
        <TemperatureID>17017</TemperatureID>
        <ConversionID>17018</ConversionID>
        <FinalConversion>193.681318681318</FinalConversion>
        <FinalPressure>116.910866910867</FinalPressure>
        <FinalTemperature>90.</FinalTemperature>
        <PreTemperatureID>17014</PreTemperatureID>
        <PreConversionID>17015</PreConversionID>
        <PrePressureID>17013</PrePressureID>
        <LibID>100257</LibID>
        <LibPosition>1002570013</LibPosition>
      </PPRElement>
    - <PPRElement ID="3457" ConCheck="1" PersistState="0">
        <Position>19</Position>
        <Flags>0</Flags>
        <Status>0</Status>
        <PressureID>17022</PressureID>
        <TemperatureID>17023</TemperatureID>
        <ConversionID>17024</ConversionID>
        <FinalConversion>190.628815628815</FinalConversion>
        <FinalPressure>117.063492063492201</FinalPressure>
        <FinalTemperature>90.</FinalTemperature>
```

FIG. 6C

```xml
- <PPRExperiment ID="298" ConCheck="1" PersistState="0">
    <CreationDate>2000/05/29 18:44:47</CreationDate>
    <CreatedBy>PPR</CreatedBy>
    <Status>0</Status>
    <ClassName>PPRExperiment</ClassName>
    <Comment />
    <Project>Polyolefins</Project>
    <Notebook>0</Notebook>
    <Flags>0</Flags>
    <Name>DV 1.2 2A</Name>
    <StartDate>2000/05/29 00:00:00</StartDate>
    <LibRows>8</LibRows>
    <LibCols>6</LibCols> LibRows
    <Log />
    <LibID>100257</LibID>
+ <Logs>
+ <PPRElements>
- <PPRModules>
    + <PPRModule ID="292" ConCheck="1" PersistState="0">
    - <PPRModule ID="293" ConCheck="1" PersistState="0">
        <Temperature>110.</Temperature>
        <TemperatureDeadband>4.</TemperatureDeadband>
        <MaxTemperature>200.</MaxTemperature>
        <StirSpeed>880.</StirSpeed>
        <Pressure>100.</Pressure>
        <PressureDeadband>2.</PressureDeadband>
        <MaxReactionTime>60.</MaxReactionTime>
        <Enabled>0</Enabled>
        - <PPRReactors>
            + <PPRReactor ID="1234" ConCheck="1" PersistState="0">
            + <PPRReactor ID="1235" ConCheck="1" PersistState="0">
            - <PPRReactor ID="1236" ConCheck="1" PersistState="0">
                <QuenchMode>By Time</QuenchMode>
                <QuenchValue>10.</QuenchValue>
            </PPRReactor>
            - <PPRReactor ID="1237" ConCheck="1" PersistState="0">
                <QuenchMode>By Time</QuenchMode>
                <QuenchValue>10.</QuenchValue>
            </PPRReactor>
            - <PPRReactor ID="1238" ConCheck="1" PersistState="0">
                <QuenchMode>By Time</QuenchMode>
                <QuenchValue>10.</QuenchValue>
            </PPRReactor>
            - <PPRReactor ID="1239" ConCheck="1" PersistState="0">
                <QuenchMode>By Time</QuenchMode>
                <QuenchValue>10.</QuenchValue>
```

FIG. 6D

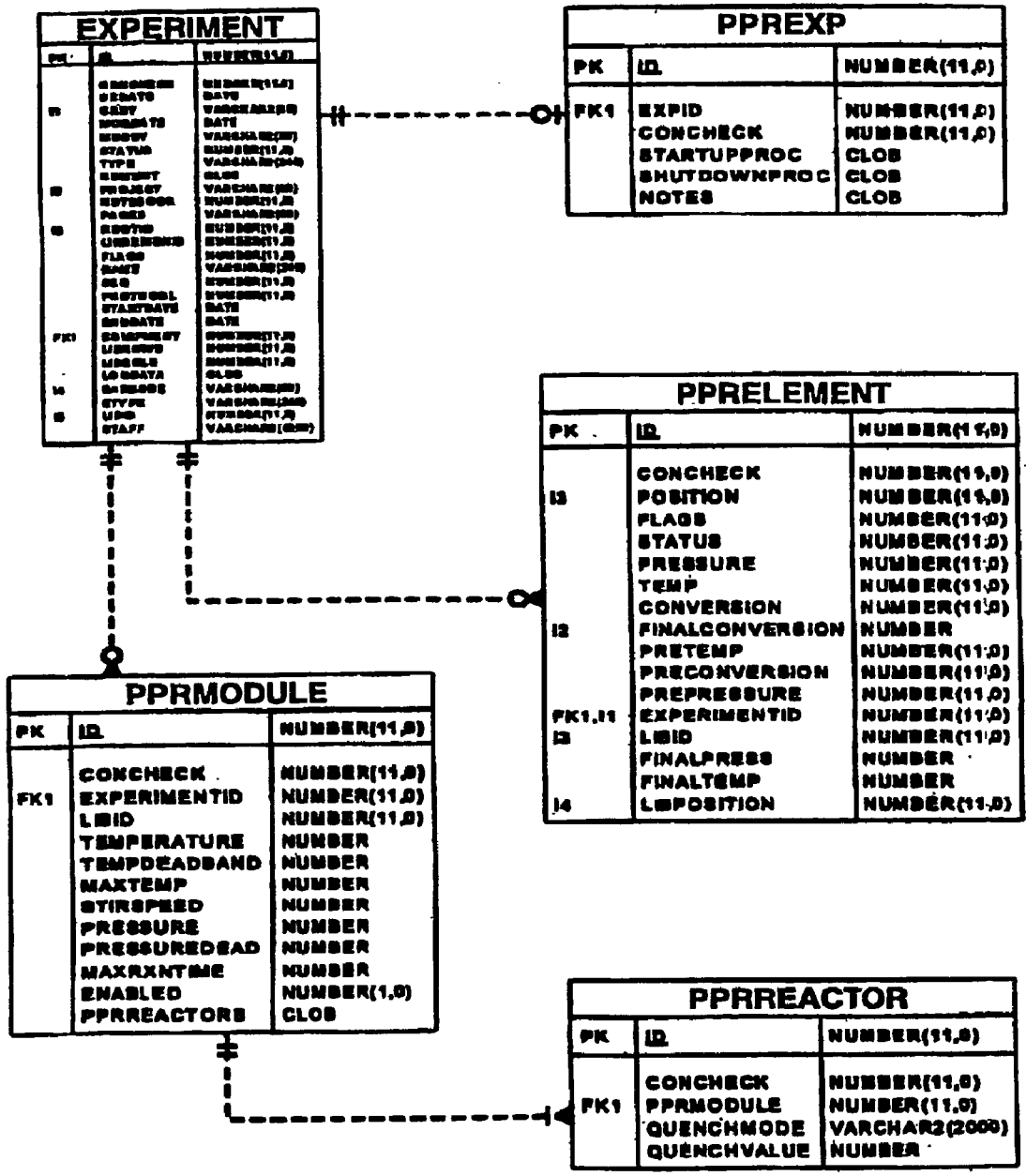
FIG._6E

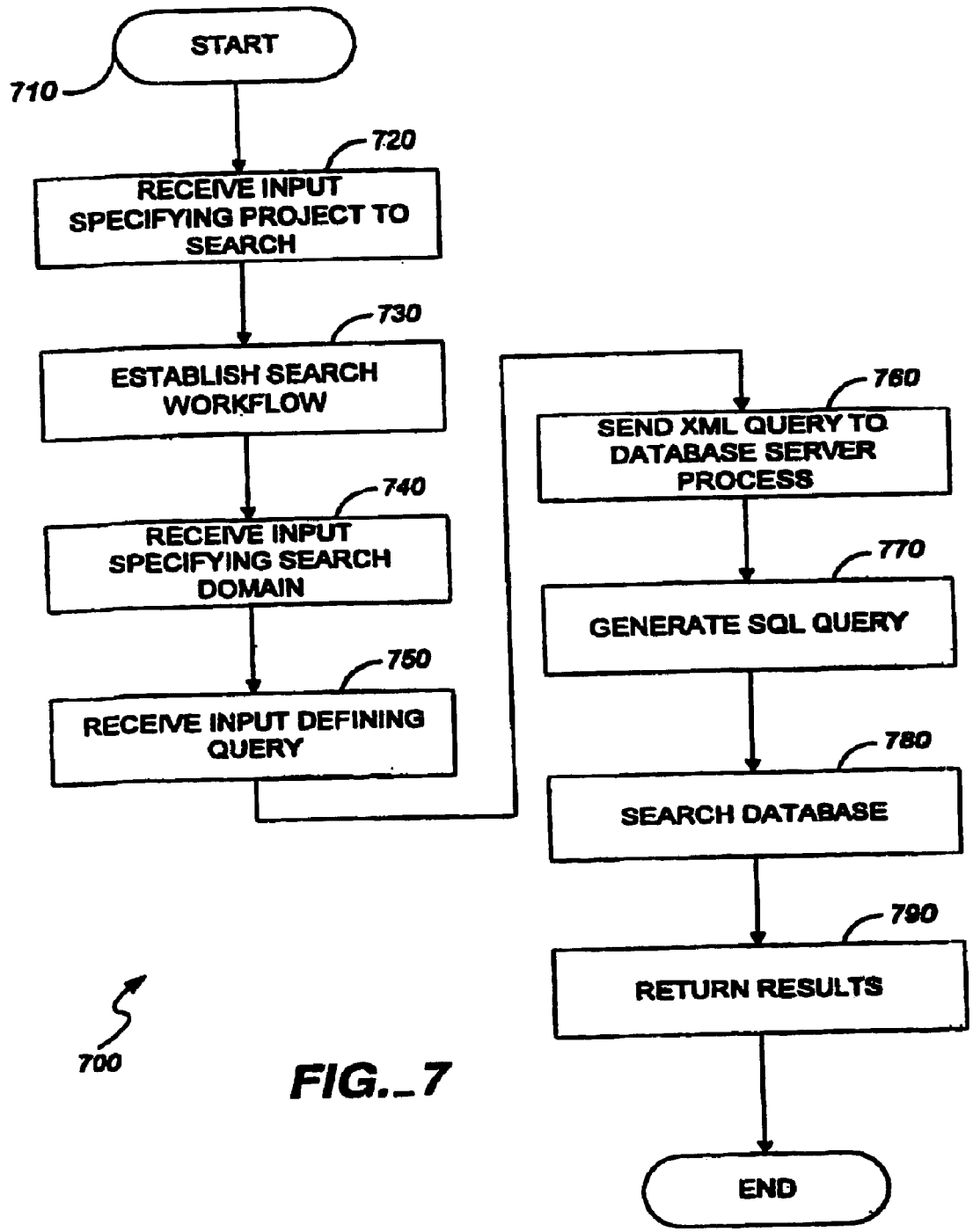
FIG._7

FIG._8A

Current Query Not Saved

Find All ○ Experiments ○ Library elements ● Other [PPR element]

| Combine | Field | Comparison | Value |
|---|---|---|---|
|  | final conversion | > | 120 |
| and | final pressure | > | 100 |
| or | final temperature | > | 130 |

[Execute Query]

FIG._8B

Queries

Available Queries

| ID | Name | Description | Created on | Created by | Modified on | Modified by | Project |
|---|---|---|---|---|---|---|---|
| 46 | MyExperiments | Query: created by = jhouston | 5/16/00 10:23:20 AM | jhouston | 5/31/00 3:28:51 PM | jhouston | Jims |
| 122 | Retention Times | retention time > 0 | 5/31/00 3:32:27 PM | jhouston |  |  | Testing |

Lists

Available Lists

| ID | Name | Description | Project | Created on | Created by | Modified on | Modified by |
|---|---|---|---|---|---|---|---|
| 176 | MyExperiments | This is a test | Testing | 5/31/00 2:06:09 PM | jhouston | | |
| 109 | Final Conversion | | | 5/30/00 2:01:18 PM | jhouston | 5/30/00 2:12:18 PM | jhouston |
| T1 | Temporary list | | | 5/31/00 6:05:46 PM | jhouston | | |

FIG._8C

Preview of Current List Data:        Number of rows to view (total 5): 10    [Refresh]

| ID | UBID | EXPERIMENT | POSITION | FLAGS | STATUS | AVGMW | AVGMN | AVGPDI |
|---|---|---|---|---|---|---|---|---|
| 264 | 100255 | 350 | 6 | | 0 | 55856.1583099242 | 48356.2753008949 | 1.1130857420008 |
| 277 | 100255 | 350 | 30 | | 0 | 36861.9734434451 | 32483.6782515549 | 1.0841951146729 |
| 290 | 100255 | 350 | 8 | | 0 | 61629.6128583621 | 52467.9791583642 | 1.1263455519794 |
| 299 | 100255 | 350 | 35 | | 0 | 41322.5296745472 | 35682.3753072569 | 1.1142186689917 |
| 302 | 100255 | 350 | 39 | | 0 | 45534.1101153839 | 40555.3254307968 | 1.0910569866657 |

FIG._8D

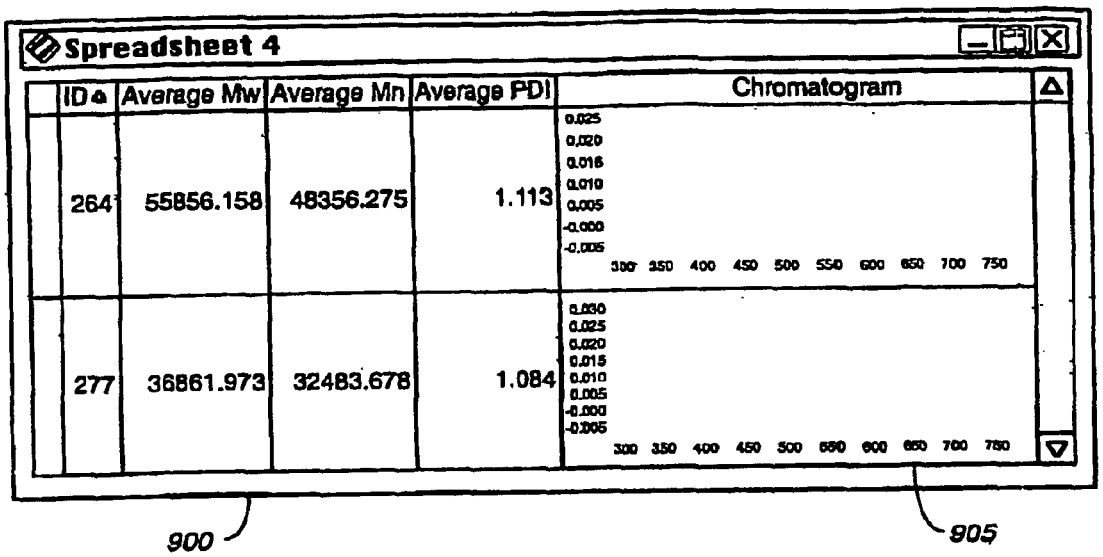
FIG._9A
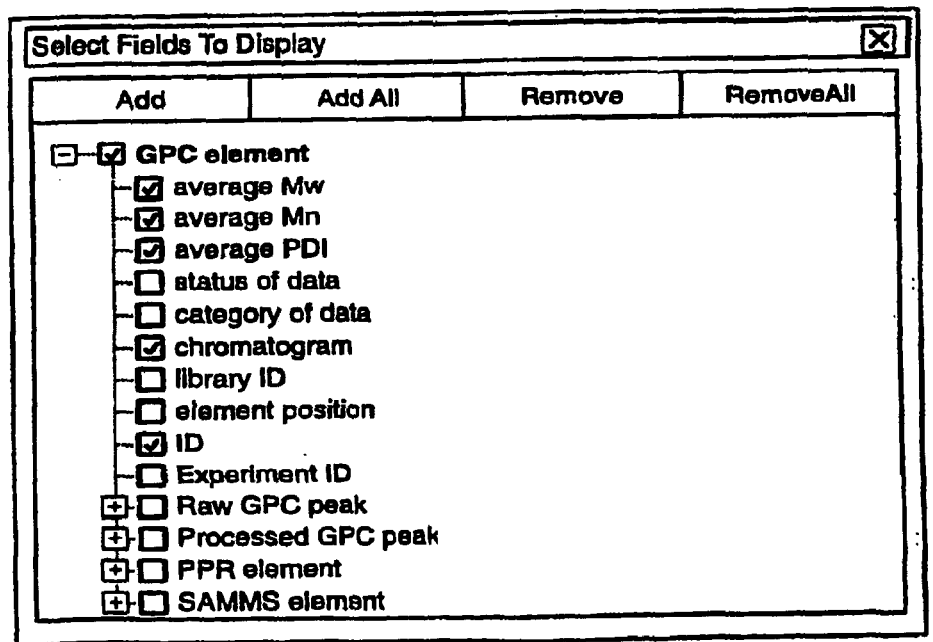
FIG._9B

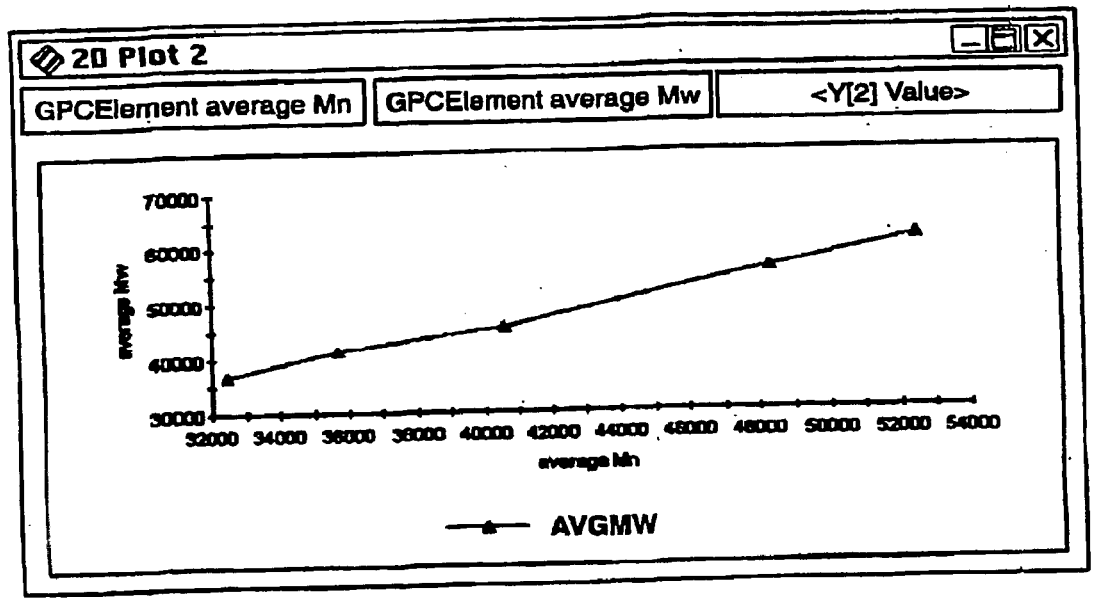
FIG._9C
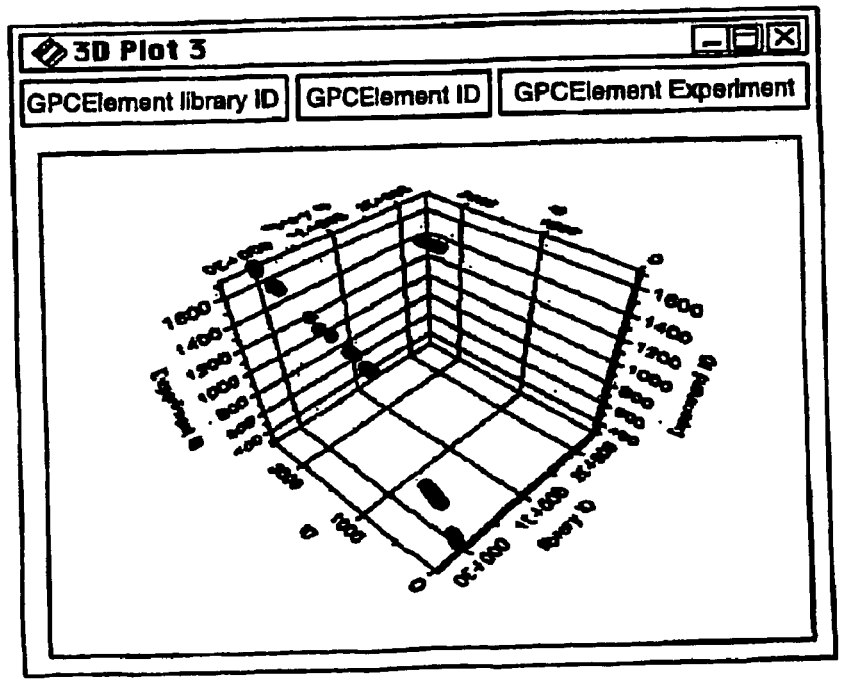
FIG._9D

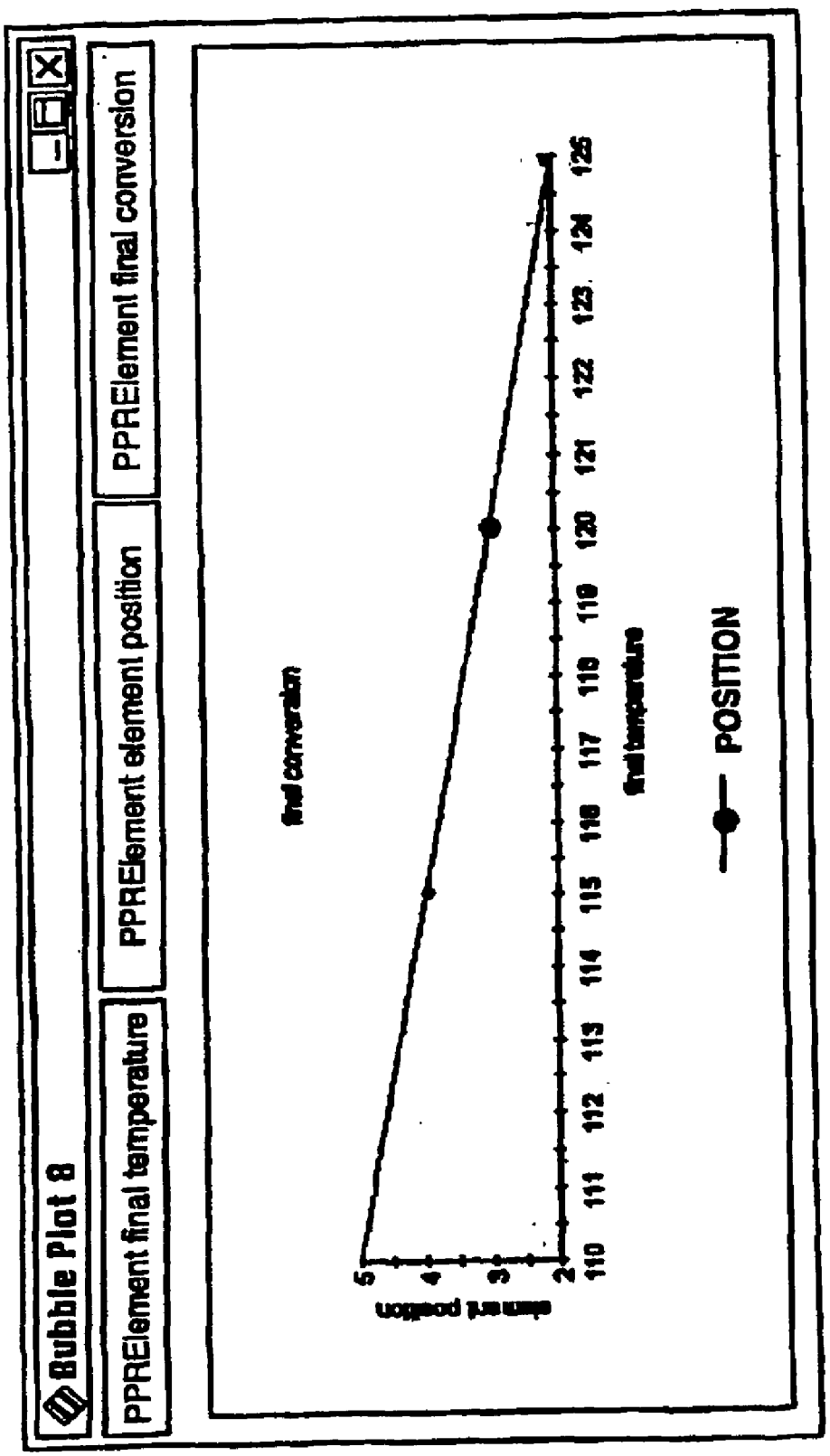
FIG._9E

LABORATORY DATABASE SYSTEM AND METHODS FOR COMBINATORIAL MATERIALS RESEARCH

CROSS-REFERENCE TO RELATED APPLICATIONS

This application is a national stage application of International Application No. PCT/US02/00466, which claims priority to and is a continuation-in-part of U.S. application Ser. No. 09/755,623, filed on Jan. 5, 2001, now U.S. Pat. No. 6,658,429. This application claims priority to those applications under 35 U.S.C. §§ 120 and 365(c).

TECHNICAL FIELD

This invention relates to database systems and methods for storing and manipulating experimental data.

BACKGROUND

The discovery of new materials with novel chemical and physical properties often leads to the development of new and useful technologies. Traditionally, the discovery and development of materials has predominantly been a trial and error process carried out by scientists who generate data one experiment at a time. This process suffers from low success rates, long time lines, and high costs, particularly as the desired materials increase in complexity. There is currently a tremendous amount of activity directed towards the discovery and optimization of materials, such as superconductors, zeolites, magnetic materials, phosphors, catalysts, thermoelectric materials, high and low dielectric materials and the like. Unfortunately, even though the chemistry of extended solids has been extensively explored, few general principles have emerged that allow one to predict with certainty the composition, structure and/or reaction pathways for the synthesis of such solid state materials.

As a result, the discovery of new materials depends largely on the ability to synthesize and analyze large numbers of new materials. Given approximately 100 elements in the periodic table that can be used to make compositions consisting of two or more elements, an incredibly large number of possible new compounds remain largely unexplored, especially when processing variables are considered. One approach to the preparation and analysis of such large numbers of compounds has been the application of combinatorial chemistry.

In general, combinatorial chemistry refers to the approach of creating vast numbers of compounds by reacting a set of starting chemicals in all possible combinations. Since its introduction into the pharmaceutical industry in the late 1980's, it has dramatically sped up the drug discovery process and is now becoming a standard practice in that industry (Chem. Eng. News Feb. 12, 1996). More recently, combinatorial techniques have been successfully applied to the synthesis of inorganic materials (G. Briceno et al., SCIENCE 270, 273–275, 1995 and X. D. Xiang et al., SCIENCE 268, 1738–1740, 1995). By use of various surface deposition techniques, masking strategies, and processing conditions, it is now possible to generate hundreds to thousands of materials of distinct compositions per square inch. These materials include high $T_c$ superconductors, magnetoresistors, and phosphors.

Using these techniques, it is now possible to create large libraries of diverse compounds or materials, including biomaterials, organics, inorganics, intermetallics, metal alloys, and ceramics, using a variety of sputtering, ablation, evaporation, and liquid dispensing systems as disclosed in U.S. Pat. Nos. 5,959,297, 6,004,617 and 6,030,917, which are incorporated by reference herein.

The generation of large numbers of new materials presents a significant challenge for conventional analytical techniques. By applying parallel or rapid serial screening techniques to these libraries of materials, however, combinatorial chemistry accelerates the speed of research, facilitates breakthroughs, and expands the amount of information available to researchers. Furthermore, the ability to observe the relationships between hundreds or thousands of materials in a short period of time enables scientists to make well-informed decisions in the discovery process and to find unexpected trends. High throughput screening techniques have been developed to facilitate this discovery process, as disclosed, for example, in U.S. Pat. Nos. 5,959,297, 6,030,917 and 6,034,775, which are incorporated by reference herein.

The vast quantities of data generated through the application of combinatorial and/or high throughput screening techniques can easily overwhelm conventional data acquisition, processing and management systems. Existing laboratory data management systems are ill-equipped to handle the large numbers of experiments required in combinatorial applications, and are not designed to rapidly acquire, process and store the large amount of data generated by such experiments, imposing significant limitations on throughput, both experimental and data processing, that stand in the way of the promised benefits of combinatorial techniques.

Basing laboratory data management systems on current relational or object-oriented databases leads to significant limitations. Those based on relational systems struggle to provide a facility for effectively defining and processing data that is intrinsically hierarchical in nature. Those based on current object-oriented databases struggle to offer the processing throughput necessary and/or may lack the flexibility of recomposition of the internal data or direct access into the internal structures of the objects as relational systems do with the relational view. Thus, there is a need for laboratory data management systems that combine the ability to process hierarchical data offered by object-oriented approaches and the processing power and/or flexibility of relational database systems.

SUMMARY

In general, in one aspect, the invention provides methods, apparatus, including computer program apparatus, and laboratory data management systems implementing techniques for processing data (including, e.g., receiving, manipulating and/or storing data) from chemical experimentation for or on a library of materials or a subset of such a library of materials. The techniques can include receiving data from a chemical experiment on a library of materials having a plurality of members and generating a representation of the chemical experiment. The representation includes data defining an experiment object having a plurality of properties derived from the chemical experiment. The experiment object is associated with the library of materials. The representation also includes data defining one or more element objects, each of which is associated with one or more members of the library of materials.

Particular implementations of the invention can include one or more of the following advantageous features. The chemical experiment can have a type that is one of a pre-defined set of one or more experiment types. The representation can implement a data model describing the set of experiment types, the data model including an experiment base class having a set of experiment base class properties including a classname property for identifying a derived experiment class and a library ID property for identifying a library of materials, and one or more derived experiment classes, each of which is associated with one of the experiment types and has a plurality of derived experiment class properties derived from the associated experiment type. The chemical experiment can be represented by a first experiment object instantiated from the derived experiment class associated with the type of the relevant chemical experiment, and by a second experiment object instantiated from the experiment base class, the classname property of the second experiment object having a value identifying the derived experiment class associated with the experiment type of the chemical experiment, and the library ID property of the second experiment object having a value identifying the library of materials. library ID property of the second experiment object having a value identifying the library of materials.

The representation can include data defining one or more data set objects or image objects. Data set objects can include sets of one or more values derived from the chemical experiment, each value being associated with one or more of the members of the library of materials. Image objects can include data representing a state of some or all of the members of the library of materials at a time during the chemical experiment. Data set objects and image objects can be associated with properties of an associated experiment object. The representation can include a self-describing representation of the chemical experiment, such as an XML string, and can also include a Java object, a COM IDL interface or a CORBA IDL interface describing the chemical experiment.

The techniques can also include parsing the representation to map the data from the chemical experiment to tables in a relational database based on the properties of an associated experiment object. Parsing the representation can include identifying each of a plurality of XML entities in an XML stream, each entity having associated content; mapping each XML entity into a corresponding object property; and assigning the content associated with an XML entity to a database table based on the corresponding object property. Derived experiment class properties can include properties derived from parameters of an associated experiment type. Data set object values can be derived from or measured for parameters of the chemical experiment, and data set objects can be associated with experiment object properties derived from the corresponding experiment parameters.

The techniques can also include storing the content in the assigned database table in the relational database, and the database can be searched to return a search result including data identifying a set of element objects satisfying search terms specified for one or more searchable fields. Search results can be stored as lists of element objects that satisfy the search terms of a query. Element object values can be displayed for one or more displayable fields. Object representations of chemical experiment data can be reconstructed from the database based on an object identifier specifying content to be retrieved from the database, from which content an object representation is generated based on a class name included in the specified content. The object representation can be mapped to an XML stream describing the content.

In general, in another aspect, the invention provides a data model for describing data from a set of pre-defined types of chemical experiments capable of being performed on a library of materials. The data model includes an experiment base class, one or more derived experiment classes, and an element class. The experiment base class has a set of experiment base class properties including a classname property for identifying a derived experiment class and a library ID property for identifying a library of materials. The derived experiment classes are associated with respective experiment types and have a plurality of derived experiment class properties derived from the associated experiment type. The element class has a plurality of element class properties including a position property for identifying one or more members of a library of materials and a value property for storing a value derived from a chemical experiment for the members identified by the position property. A specific experiment in the set of pre-defined experiments is represented by a first experiment object instantiated from the derived experiment class associated with the type of the chemical experiment, and by a second experiment object instantiated from the experiment base class. The classname property of the second experiment object has a value identifying the derived experiment class associated with the experiment type of the chemical experiment, while the library ID property of the second experiment object having a value identifying the library of materials.

Advantages that can be seen in implementations of the invention include one or more of the following. Decoupling of client processes from the database isolates the experimental process from the underlying data storage, which means that client processes may be extended without requiring immediate extension of the database schema, and/or that the database is protected from unintended and/or unauthorized alteration by client processes. The database can be extended and remain backward compatible with existing client processes. Data is persisted in a human-readable format, aiding in error diagnosis. Using a common schema to store data describing different experiment types means that objects representing experimental data can be recomposed across technical disciplines.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 illustrates a user interface for creating a library.

FIGS. 4A–4B illustrate a portion of an XML document defining a data object representing an experimental data set and a relational database table into which such an object is mapped, respectively.

FIGS. 5A–5B illustrate portions of an XML document defining a data object representing an instrumentation procedure for a materials-handling apparatus.

FIG. 5C illustrates a relational database table into which the data object of FIGS. 5A–5B is mapped.

FIGS. 6A–6D illustrate portions of an XML document defining a set of data objects representing a polymerization experiment.

FIG. 6E illustrates a set of relational database tables into which the set of objects of FIGS. 6A–6D is mapped.

FIG. 7 is a flow diagram illustrating a method for retrieving data from a database.

FIGS. 8A–8D illustrate user interfaces for constructing a query and viewing query results.

FIGS. 9A–9E illustrate user interfaces for viewing data retrieved from a database according to the invention.

Like reference symbols in the various drawings indicate like elements.

DETAILED DESCRIPTION

Figure 1:
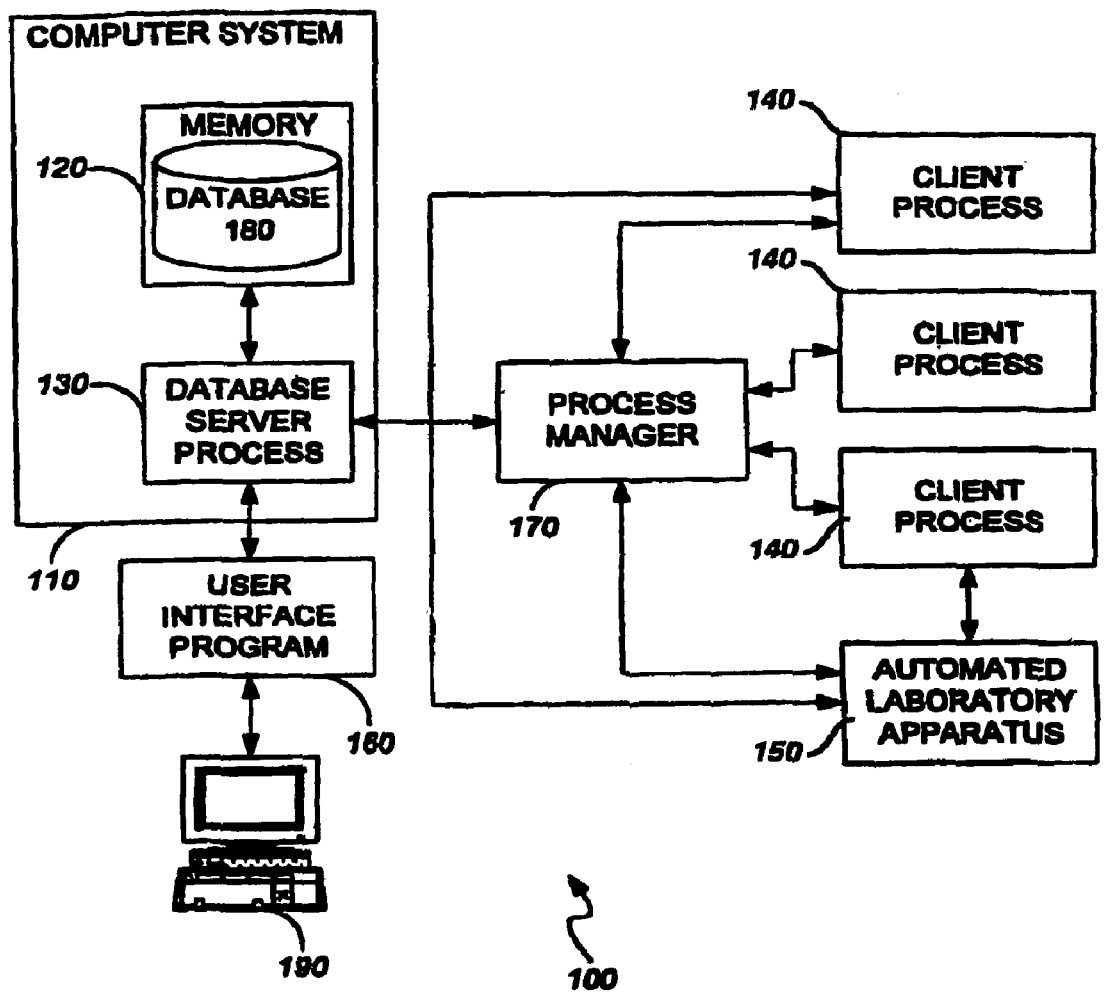
FIG. 1 is a block diagram illustrating a laboratory data management system including a database server process according to the invention.

FIG. 1 illustrates a laboratory data management system 100 that includes a general-purpose programmable digital computer system 110 of conventional construction including a memory 120 and a processor for running a database server process 130, and one or more client processes 140. As used in this specification, a client process is a process that uses services provided by another process, while a server process is a process that provides such services to clients. Client processes 140 can be implemented using conventional software development tools such as Microsoft® Visual Basic®, C++, and Java™, and laboratory data management system 100 is compatible with clients developed using such tools. In one implementation, database server process 130 and client processes 140 are implemented as modules of a process control and data management program such as that described in U.S. application Ser. No. 09/550,549, filed Apr. 14, 2000, which is incorporated by reference herein.

Optionally, client processes 140 include one or more of automated or semi-automated laboratory apparatuses 150, a user interface program 160 and/or a process manager 170 for controlling laboratory apparatus 150. Database server process 130 is coupled to a database 180 stored in memory 120. In one implementation, database server process 130 and client processes 140 are implemented as computer programs stored on computer-readable media, and can be distributed across multiple computers. Optionally, laboratory data management system 100 also includes input/output devices 190 and conventional communications hardware and software by which computer system 110 can optionally be connected to other computer systems by a computer network, such as a local area network, wide area network or the Internet.

In general, laboratory data management system 100 receives data from client 140 for storage, returns an identifier for the data, provides a way of retrieving the data based on the identifier, provides the ability to search the data based on the internal attribute values of the data, and the ability to retrieve data from the these queries in a number of different ways, generally in tabular (e.g., in a relational view) and object forms.

Laboratory data management system 100 is configured to manage data generated during the course of the experiments performed by laboratory apparatus 150. An experiment is performed on a library of materials. As used in this specification, a library of materials is a matrix having two or more members, generally containing some variance in chemical or material composition, amount, reaction conditions, and/or processing conditions. A member, in turn, represents a single constituent, location, or position in a library containing one set of chemicals or materials subject to one set of reaction or processing conditions. While this specification uses specific types of experiments as examples, the particular materials, compounds or chemistries involved are not critical; instead, the methods, computer programs and systems described are broadly applicable to a wide variety of library types and chemistries. Thus, in particular implementations, libraries used in system 100 can include, for example, libraries of biomaterials, organics, organometallics, inorganics, intermetallics, metal alloys, or ceramics, and in particular heterogeneous and homogeneous catalysts, specialty application polymers and formulations of organic and inorganic materials including, for example mixtures of polymers and/or bioactive materials with any other materials. Such libraries can be employed in experiments directed to the discovery of new and useful compositions, such as superconductors, zeolites, magnetic materials, phosphors, catalysts, thermoelectric materials, high and low dielectric materials, and other materials of interest. Experiments on such libraries can involve the measurement of a variety of properties, including without limitation electrical, thermal, mechanical, morphological, optical, magnetic, chemical, conductivity, superconductivity, resistivity, thermal conductivity, anisotropy, hardness, crystallinity, optical transparency, magnetoresistance, permeability, frequency doubling, photoemission, coercivity, dielectric strength, or other useful properties that will be apparent to those of skill in the art, and can yield data in the form, for example, electrical voltages and resistivity, photon counts, and frequency and wavelength of electromagnetic radiation, any of which could be measured on a time-varying basis or as a combination of each other in the form of dependent-independent variables.

Libraries can include physical arrays of materials, with different materials located at different regions of a substrate. In one implementation, each, library includes one or more members, each of which may be represented as a region in an arrangement (e.g., an array) of one or more regions. A library can include two or more members, preferably four, ten, twenty, or even ninety-six or more members. The members of a library may, but need not necessarily, correspond to locations on a physical substrate (such as a microtiter plate, wafer or the like) on which the library was or will be created. However, while the library may correspond to the geometry of the ultimate physical substrate, it may also represent a collection of library members on a more conceptual level. Conventionally, libraries may be depicted as square or rectangular arrays. However, libraries can be represented or prepared in any convenient shape, such as square, rectangle, circle, triangle or the like, and in one, two or three dimensions, depending, for example, on the underlying chemistry or apparatus involved. Details of library design and preparation are further discussed in co-pending U.S. application Ser. No. 09/420,334, filed on Oct. 18, 1999, and in U.S. Pat. No. 5,776,359, U.S. Pat. No. 5,959,297, U.S. Pat. No. 5,985,356, U.S. Pat. No. 6,030,917, U.S. Pat. No. 6,034,775, and U.S. Pat. No. 6,149,882, each of which is incorporated by reference herein.

An experiment need not be performed on all members of a library, but may be performed on one member or a subset of members in the library. As used in this specification, an experiment can include using instruments to create or manipulate samples and/or gather data, as well as processing (or reprocessing) data gathered during previous experiments. In one implementation, experimental data (whether measured directly or derived indirectly from measured data) can be represented in system 100 as a XYDataSet object, a data structure holding values measured or derived for one or more members of a library of materials—for example, an array having an element for each member in a corresponding library of materials (or a subset of those members), with each array element having a value corresponding to a measured or derived experimental value for the corresponding library member. Data can also be represented as an Image object, a two-dimensional, time-fixed data set representing the state of a library at a particular time, such as a spectrogram or photograph of a physical substrate embodying a library at a particular point in time.

Laboratory apparatus 150 can include any automated or semi-automated device for handling or processing materials, gathering experimental data or analyzing chemical properties, such as synthesis or analysis robots, pumps, temperature or pressure controllers, reactors, digital cameras for visible or infrared imaging, evaporative light scattering detectors, microcalorimetry arrays and the like. Exemplary apparatus 150 for material processing and screening are disclosed in U.S. Pat. No. 5,776,359, U.S. Pat. No. 5,959, 297, U.S. Pat. No. 5,985,356, U.S. Pat. No. 6,030,917, U.S. Pat. No. 6,034,775, and U.S. Pat. No. 6,149,882, previously incorporated by reference herein, as well as PCT publications WO 00/09255, WO 00/51720, and WO 00/36410, each of which is incorporated by reference herein. Optionally, apparatus 150 are controlled by an automated instrument control software application such as that described in U.S. Pat. No. 6,507,945, which is incorporated by reference herein.

Database 180 stores experimental and analytical data derived from experiments performed by laboratory data management system 100. In one implementation, laboratory data management system 100 maintains three representations of each item of data: an object representation; a self-describing persistent representation and a representation based on relational tables.

Figure 2:
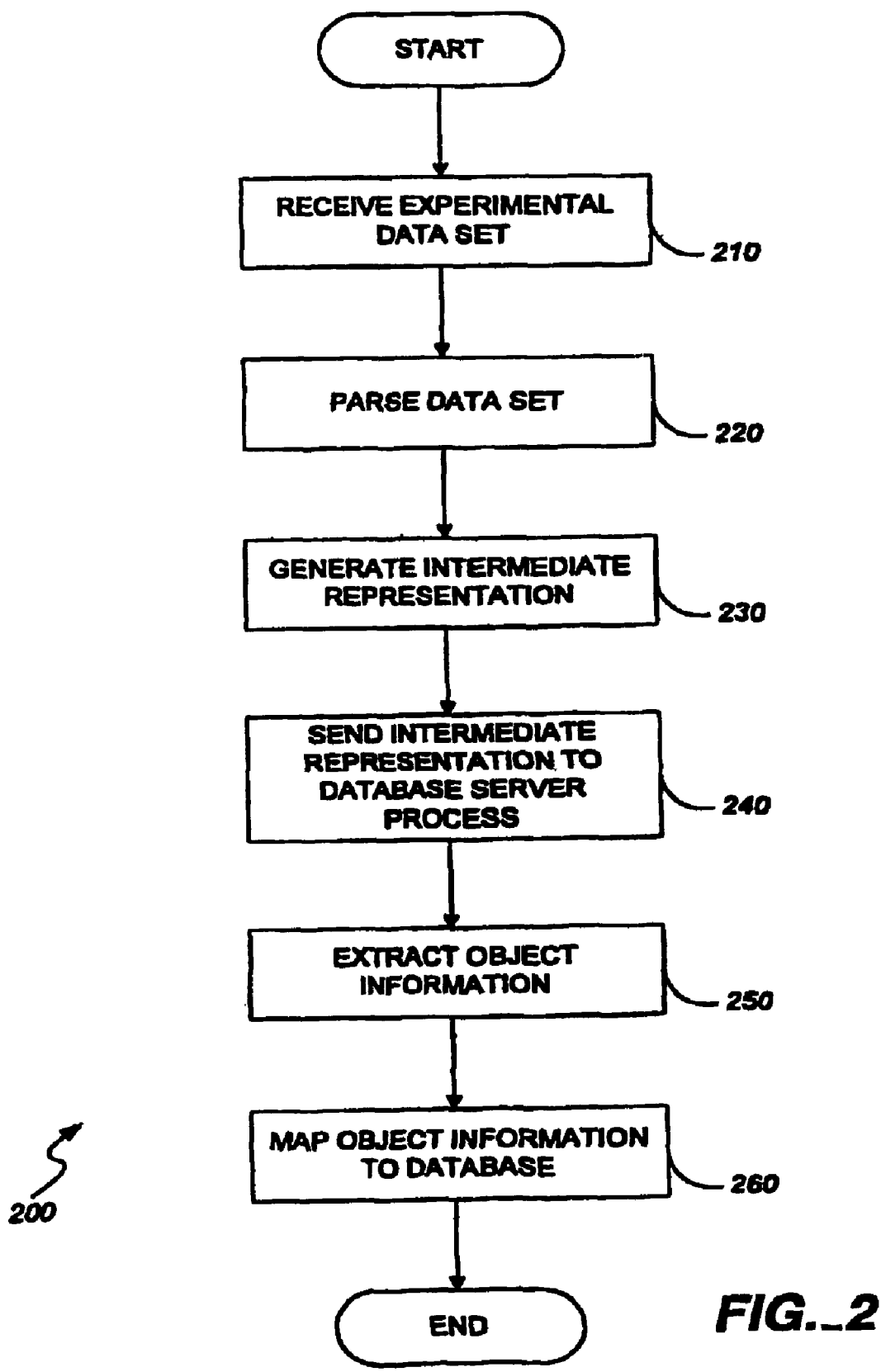
FIG. 2 is a flow diagram illustrating a method for storing data from an experiment.

A method 200 for storing data from an experiment performed by laboratory apparatus 150 is illustrated in FIG. 2. The method starts when process manager 170 receives from laboratory apparatus 150 a set of data derived from the experiment (step 210)—for example, a set of gel permeation chromatograms measured for each of the members in a library of polymers. Process manager 170 parses the data set (step 220), e.g., to associate individual data values with their corresponding library members, and packages the data for transmission to database server process 130, such as by generating an XML stream containing the data and associated mark-up identifying the type of data and its association with the members of the corresponding library of materials (step 230). Process manager 170 then sends database server process 130 a database access request including the packaged data (step 240).

Database server process 130 parses the data, extracting for each object represented in the XML stream an object type and optionally one or more associated object properties (step 250), as will be described in more detail below. Database server process 130 uses the extracted object information to store (at least temporarily) each object in the stream in database 180 (step 260)—for example, by mapping each object to one or more database tables according to a mapping schema implemented in database server process 130.

In some implementations, system 100 can support multiple schema for mapping experimental data (e.g., in XML form) into one or more alternate logical representations in relational form. The mapping can be partial—for example, loading a subset of the experimental data into relational tables. Alternate mappings can be used to support different applications of the data in relational form. For example, one mapping can be used to populate a specific set of tables with experimental data in such a way as to optimize a certain set of searching or analytical systems, including but not limited to the method 400 of retrieving data described herein. Additional mappings can be added to populate tables for the purpose of experimental documentation. Similarly, two equivalent mappings can be used to provide a means of populating a back-up database.

In one implementation, client processes 140 interact with experimental data generated in system 100 through an object model representing experiments performed by system 100, illustrated in FIG. 3. In this object model, every experiment performed by system 100 is represented by an Experiment object 330 having a set of associated properties and methods that represent the experiment. Each Experiment object 330 is associated with a particular library of materials 300—for example, by virtue of an associated LibraryID 320 (here represented as a barcode), assigned when the library is created, that uniquely identifies the library in the universe of libraries defined for an instance of system 100.

The user registers a new library in system 100 by requesting a new LibraryID for the new library. In response to the request, database server process 130 generates a LibraryID for the new library, and defines a library geometry for the library—for example, by prompting the user to input the number of rows and columns in the new library. Optionally, the user can also specify values for one or more searchable fields for the library, including a library name, project name, notebook and page numbers, start and end dates, comments and keywords to be associated with the new library by making appropriate entries in fields provided by user interface program 160. The user can also provide information about the library to other users by specifying a status for the new library, such as "In progress", to specify, e.g., that synthesis of the library is underway, "Invalid" or "Questionable", to denote problems with the library, "Released", to specify that the library is available for use by other users of system 100, and "Archived", to reflect, e.g., that the library has been sent off-site for storage, to name just a few. Finally, the user can also associate one or more data files with the new library by specifying the desired files through user interface program 160. When it has received the necessary information, database server process 130 creates an Experiment object representing the preparation of the library—e.g., a Synthesis object, as described below. Optionally, database server process 130 can also create a separate object representing each new library (such as, for example, a Library object having properties specifying, e.g., LibraryID, library geometry, the identity of materials making up the library and the like). After creating the appropriate data structure or structures to represent the new library, database server process 130 records identifying information in database 180—for example, by updating a master concordance table in database 180 to associate the new library with a project identified by the specified project name.

One implementation of a generic Experiment object 330 can include the following properties in addition to LibraryID 320: ExperimentID, which is a number uniquely identifying the experiment within system 100; CreationDate, which is a date reflecting the date of the underlying experiment; CreatedBy, a string identifying the user who performed the experiment or created the Experiment object; Notebook, which is an integer identifying the laboratory notebook in which the experiment is recorded; Keywords, which are strings specifying searchable terms identifying the experiment; and the like.

Experiment subclasses (or derived Experiment classes) can be defined to correspond to one or more specific types of experiments capable of being performed by system 100. Thus, for example, a parallel pressure experiment can be represented by a derived PPRExperiment class that inherits the properties of the base Experiment class and has additional experiment-specific properties such as XYDataSet objects holding measured or derived values for pressure, temperature, conversion for each element or member of a library of materials. Similarly, a gel permeation chromatography experiment can be represented by a GPCExperiment subclass that, in addition to the properties of the base Experiment class, has additional experiment-specific properties such as a XYDataSet object storing chromatograms measured for each library element or member. In general, derived Experiment classes can be defined to describe any type of experiment capable of being performed on a library of materials by apparatus 150 associated with system 100.

In one implementation, each library 300 is represented by at least one Experiment object 330, including a Synthesis object (instantiated from a Synthesis subclass of the Experiment base class) reflecting the library's preparation. In addition to properties inherited from the Experiment base class, a Synthesis object has additional properties denoting the library's geometry (e.g., the number of rows and columns in the matrix representing the library of materials), and may also have properties corresponding to the methods used to prepare the library, such as data for reagents, processing conditions and the like. Additional experiments performed on the same library can result in multiple Experiment objects representing (e.g., referring to) the library. Optionally, experiments that result in reformulation or other alteration of the library (e.g., experiments that would result in a significantly different composition of matter and/or phase) can result in the creation of a new library.

An Experiment object 330 can (but need not necessarily) also include a collection of Element objects 340 representing individual members 310 of library 300. Each Element object 340 represents a particular material in library 300 on which an experiment is to be or has been performed, and is characterized by a Position property, identifying the particular member 310 of the library, and a Value property containing a measured or derived data value for that library member. In one implementation, Element objects can be hierarchical children of a parent Experiment object, and can, for example, be referenced as individual children in a collection child attribute of the parent Experiment object. However, Element objects (and the experimental data they contain) can also be retrieved and manipulated independently of their parent Experiment.

Database 180 can also store other objects, including, for example, database queries and lists (described in more detail below), as well as a collection of pre-defined objects and object prototypes available for process manager 170 to use to control laboratory apparatus 150, as described in commonly-owned co-pending U.S. application Ser. No. 09/550,549, filed Apr. 14, 2000, which is incorporated by reference herein.

Each object has a set of properties that can include, e.g., object metadata, attributes and joins. Object metadata includes information defining the object class, such as an object description, an object type (e.g., Experiment, Element, Other), and a choice of a set of flags, such as Queryable, Updateable, Insertable, Common, and Retrievable in Recordset, that can be assigned to instances of the object class by a user. Object attributes include the set of properties that can be assigned values for any given instance of the object. Each attribute may be described, e.g., by name, description, the type of data the attribute stores (for example integer data, floating point, text strings, image, or x-y data), and other properties such as whether the data is user or system assigned, if it can be updated, if it can be retrieved in a tabular representation of the object type or only through the full object representation, and if the attribute should be presented to the user as having a vocabulary of permitted values, either specific fixed values or those from the current set of instances of the object stored. Finally, object joins specify the relationships between the object and other objects available to system 100, such as the names of any parent or child objects and attributes of those objects.

Communication between client processes 140 and database server process 130 is provided through a persistent representation of data in a self-describing extensible format such as XML. As described above, client processes 140 receive or generate data derived from an experiment and package that data using known techniques in a format (e.g., an XML data stream) for communication to database server process 130. Upon receiving such a communication from a client process 140, database server process 130 parses the incoming data stream to extract object descriptions from the data stream. In one implementation, an object type corresponds to a top-level entity in the XML data stream, while sub-entites in the stream map to properties of the respective objects. For example, each top-level XML entity may have a name that corresponds to an object type defined in the metadata of database 180. The sub-entities of each top-level entity then map to properties defined for the corresponding object, for example by sub-entity name. In this implementation, some entities may map to simple object properties, such as strings, longs, doubles, etc., while others may map to sub-objects or collections of sub-objects. Basic object properties that database server process 130 needs to store an object in database 180 in step 260 may be included as attributes set out in the XML tag that includes the entity name.

Database server process 130 maps the extracted experimental data into tables in relational database 180 (which can be implemented in any commercially available relational database, such as those offered by Oracle®, Sybase®, Informix®, IBM® or the like) according to a predetermined mapping schema In one implementation, database server process 130 maps classes (e.g., the Experiment class and any subclasses, the Element class, etc.), to database tables, with each row representing an individual instance of the class or classes in the table (e.g., an experiment identified by a unique ExperimentID) and columns corresponding to class properties (e.g., for an experiment, the individual ExperimentID primary key, project name, experiment name, notebook number or the like, although not all properties need necessarily be saved in database 180).

The following example illustrates the communication of an Experiment object from a client process 140 to database server process 130 to database 180. After performing a particular experiment, a client process 140 generates the following XML code:

```
<Experiment ID="0" ConCheck="0" PersistState="1"
UserID="jsmith">
    <Project>test</Project>
    <Status>6</Status>
    <Notebook>1</Notebook>
    <Pages>1-5</Pages>
    <Flags>0</Flags>
    <Name>simple test</Name>
    <Keywords>
        <Keyword ID="0" ConCheck="0" PersistState="1"
UserID="jsmith">
            <Value>keyword 1</Value>
        </Keyword>
        <Keyword ID="0" ConCheck="0" PersistState="1"
```

-continued

```
UserID="jsmith">
        <Value>keyword 2</Value>
      </Keyword>
    </Keywords>
    <Attachments/>
    <XML Attachments/>
  </Experiment>
```

By sending this XML stream to database server process 130 in step 240, process manager 170 requests database server process 130 to save a new Experiment object (a save request is indicated because the specified ID for the object is "0"; a request to modify or delete an existing Experiment object would include a previously-defined Experiment ID) for the user identified by UserID "jsmith". The Experiment object to be saved has been assigned the name "simple test", is part of a project called "test", and is associated with pages 1 through 5 of notebook number 1. The object has two Keyword sub-objects, "keyword 1" and "keyword 2". Although the Experiment object definition provides for the association of Attachment and XML Attachment sub-objects with each experiment, none are provided for the "simple test" experiment in this instance.

Assuming the user "jsmith" has appropriate system authorization, after parsing this object in step 250, database server process 130 assigns an Experiment ID and Keyword IDs and in step 260 stores the information as follows (in EXPERIMENT and KEYWORD tables) in database 180:

| EXPERIMENT ID | PROJECT | NAME | NOTEBOOK | PAGES |
|---|---|---|---|---|
| 999 | test | simple test | 1 | 1–5 |

| KEYWORD ID | EXPERIMENT ID | VALUE |
|---|---|---|
| 222 | 999 | keyword 1 |
| 223 | 999 | keyword 2 |

As discussed above, experimental data can be parsed into multiple database representations. Thus, for example, database 180 can include a set of tables comprising a relational schema, with the tables being designed to record the progress of multiple different experiments performed on a library. For this purpose, each experiment can be stored as a separate row in a generic Experiment table, with columns for the date, library ID, project, specific experiment type, etc. as described above. The experiment-specific data can then be stored in separate experiment-specific tables.

The tables below illustrate a representation of the data in the relational database resulting from the processing of two screening experiments into a relational schema built for the above purposes:

| EXPERIMENT ID | LIBRARY ID | PROJECT | NAME | NOTE-BOOK | PAGES |
|---|---|---|---|---|---|
| 1 | 1 | test | screen 1 | 1 | 1–5 |
| 2 | 2 | test | screen 2 | 1 | 5–7 |

SCREEN1

| EXPERIMENTID | TEMPERATURE | RESULT |
|---|---|---|
| 1 | 40 | 2.0 |
| 2 | 35 | 2.2 |

SCREEN2

| EXPERIMENTID | RESULT |
|---|---|
| 1 | 25.3 |
| 2 | 35.4 |

At the same time, system 100 can support a second a set of tables comprising a relational schema designed for the purpose of correlating a set of experimental facts across a specific library. For this purpose, the table design can include the library screening data directly within the main table, thus allowing for direct retrieval of screening data without the need for a query involving multiple tables.

The table below shows a representation of the data in the relational database resulting from the processing of the two screening experiments discussed immediately above into a relational schema built for this purpose (some fields in the EXPERIMENT table have been omitted for clarity):

| EXPERIMENT ID | LIBRARYID | SCREEN1TEMP | SCREEN1RESULT | SCREEN2RESULT |
|---|---|---|---|---|
| 1 | 1 | 40 | 2.0 | 25.3 |
| 2 | 2 | 35 | 2.2 | 35.4 |

The process of parsing the intermediate representation and mapping that representation to tables in database 180 (steps 250 and 260 above) will now be described in more detail by reference to additional specific examples. In one implementation, database server process 130 extracts object information from an XML data stream and uses that information to create objects (e.g., Java objects) from the XML stream. The main external entry point for storing (insert or update) objects in database 180 can be implemented as a method public long Save (String xml), exemplified in Java code Listing 1, below.

This method accepts a string containing the XML representation of the object and returns the resulting ID of the object (>0) or an error code (<=0). The overall process is to create and map the data from the XML document into objects (singular or plural, which may be implemented in known programming languages such as Java, Eiffel and/or the COM or CORBA interface definition languages), then store the contents of the objects using, e.g., a commercial Java class package, such as version 2.0 of the Visual Business Sight Framework (VBSF), available from Objectmatter, Inc. (http://www.objectmatter.com). Although this example is discussed in the context of Java objects and the Objectmatter class package, the particular programming language and/or class package used is not critical to the invention. Preferably, the XML stream is not exposed to any dependency or use of the class package capabilities, which therefore need not limit or influence the design and construction of XML documents representing objects. It is expected that the specific implementation of the storage of the objects could change with no impact on the experimental object design, the XML document representation of the objects, the interface of database server process 130, or the use of a relational database for the final data storage. Thus, for example, database server process 130 can be configured to map experimental data directly from the XML representation into database 180 (e.g., using known software packages for mapping XML documents into relational databases).

The Save method loads the XML stream into an XML parser, which may be any commercial XML document object model (DOM) parser such as the Microsoft XML parser available with Internet Explorer 5.01, supplemented by wrappers implemented here as an additional separate class clientutilities.XMLHelper and the interface clientutilities.IXMLEntity representing an individual entity in the XML document. Once the root object of the XML stream has been obtained, the SaveXML method begins the process of constructing a Java object from the XML stream.

If the request is to save an object with a non-zero ID, the XMLNodeToObject method that SaveXML calls creates a corresponding Java object and retrieves the specified object data from the database. If the object does not exist or the ID is 0, the XMLNodeToObject method simply returns the new Java object. SaveXML then compares the value of the ConCheck attribute in the incoming XML stream and that of the database. If these values are not equal, this indicates that the client is attempting to update an object using an out of date set of data and a "concurrency check" failure is returned. The ConCheck value is incremented with each successfully update of an object, reflecting its use as an object version number.

Once the initial data or newly initialized Java object has been created, SaveXML processes each child XML entity of the object, attempting to map the XML node into an object attribute, a sub-object reference, or a collection of sub-objects. This is accomplished in the ReadXMLNode( ) method discussed below.

Once the XML entity nodes have been processed, if the object has a ClassName attribute, the SaveXML method stores the name of the Java class/XML object being saved into that attribute. This supports hierarchies of persistent objects where the storage is divided among several tables— that is, the storage is essentially a process of storing the base class attributes followed by storage of the derived class attributes, as in the example of the design of a PPRExperiment object to capture a polymerization reactor experiment using the Experiment object as a base class. This is discussed in more detail below.

The ReadXMLNode method first determines if the requested operation is a deletion or a nullification of the node data and handles those special requests. It then attempts to find a best match for the XML entity node against the properties of the Java object being stored by examining the first sub-entity name. In the XML DOM, an entity with only data has a single sub-node with the name "#text". If this is found as a sub-node, this is interpreted as the simple case of a mapping of an XML node to directly to a Java class field, and the value of the XML node is used to set the value of the Java class field.

If the XML entity node has something other than a simple text value, the matching Java class field is obtained as guidance for how to process the XML sub-entities. A test is made to determine if the Java class field is a String field, and if so, the entire sub-entity stream is stored whole into a single Java field.

This test permits the assignment of an arbitrary section of the XML document into a single Java field and subsequently a relational table column, permitting a short-cut whereby each XML entity is not required to be mapped into a specific relational table column. This may be advantageous where a section of the XML document is expected to change frequently as the result of iterations of software, instrument, or laboratory workflow development, adding or modifying the experimental data stream. This may also be useful where a section of the XML document does not represent data that would be commonly searched by attribute value, but where the section must be stored in whole for documentation purposes, such as the storage of an automated materials-handling procedure discussed below.

If the Java field is a collection or reference attribute (e.g., from the Objectmatter class package), the XML entity node is processed as a collection of sub-objects or a contained single sub-object. This is done recursively to permit the arbitrary nesting of objects or collections of objects within other objects, which is important in the representation of intrinsically hierarchical data such as laboratory experimental data.

In one implementation, it is useful (although not necessary to the invention) to use the Experiment object as a base class for all experiments. This provides several benefits, including:

1. The traditional object-oriented design benefit of improving reusability in the sense that this base class identifies the common attributes for all laboratory experiments.

2. The ability to use the Experiment object itself to determine and represent the time-ordered sequence of all laboratory experiments related to a combinatorial library.

The first benefit means that since the Experiment object contains attributes common to all experiments (such as library ID, date and time, notebook number and page, staff member, and keywords), it is possible to simply query the database for all experiments performed on a given library (for example) and immediately produce a list.

The second benefit is more significant in the overall design of the system: since the actual name of the specific Experiment-derived class is stored using the ClassName attribute in the SaveXML method as described above, it is possible to dynamically retrieve the specific experimental detail for any type of experiment by simply inspecting the value of the Experiment.ClassName property retrieved and using that name in a subsequent GetObject request. This permits the construction of universal user software that can view any experimental data records from the past, present and future definitions of experiment objects.

Figure 4A:
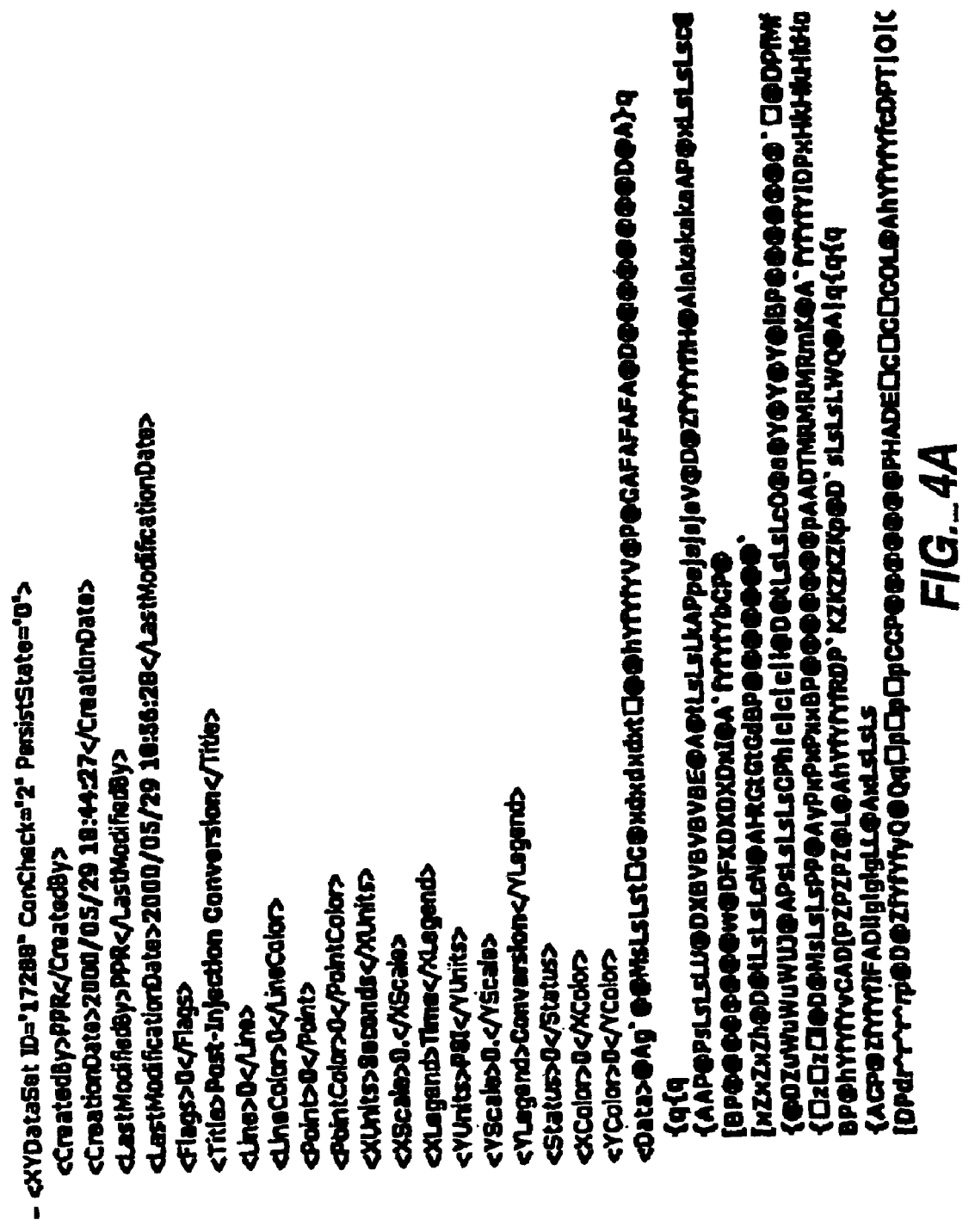

FIG. 4A illustrates a portion of an XML document representing an XYDataSet object representing data from post catalyst injection measurements on a reactor in the Parallel Polymerization Reactor (PPR)™ system developed by Symyx Technologies, Inc. of Santa Clara, Calif. As discussed above, such objects can be used to represent data taken from a large variety of different sources, including electrical, temperature and pressure sensors and general analog/digital signals. The data, which is a set of IEEE 8 byte floating point numbers, is encoded in the UTF-8 character set in the XML document in accordance with the rules on character sets permitted in XML documents.

Database server process 130 first maps the XYDataSet object represented by the XML document of FIG. 4A into an instance of the Java class whose fields are defined as follows:

```
public class XYDataSet {
    public Long ID;
    public Long ConCheck;
    public String CreatedBy;
    public Date CreationDate;
    public String LastModifiedBy;
    public Date LastModificationDate;
    public byte[] Data;
    public Long Flags;
    public String Title;
    public Long Line;
    public Long LineColor;
    public Long Point;
    public Long PointColor;
    public String XUnits;
    public Double XScale;
    public String XLegend;
    public String YUnits;
    public Double YScale;
    public String YLegend;
    public Long Status;
    public Long XColor;
    public Long YColor;
    public Double SuggestMinX;
    public Double SuggestMaxX;
    public Double SuggestMinY;
    public Double SuggestMaxY;
    public Long PlotStyle;
    public Double XDataStart;
    public Double XDataInterval;
    public byte[] YData;
    public byte[] XData;
}
```

Database server process 130 them maps this Java class into the Oracle table shown in FIG. 4B.

FIGS. 5A–5B illustrate portions of an XML document defining an instrumentation procedure implemented for Impressionist™ materials-handling software available from Symyx Technologies, Inc. of Santa Clara, Calif. As described in U.S. application Ser. No. 09/305,830, filed on May 5, 1999, the Impressionist software can be used to control a large number of laboratory devices used in experimentation (synthesis and screening). To that end, Impressionist can use XML documents to save definitions of instrumentation resources, working substrates, and experimental procedures. Laboratory data management system 100 can then be used as a storage repository for all three of these XML documents. The example of FIGS. 5A–5B illustrate the processing of a procedure definition embodied in an Impressionist_Procedure_1 object.

One challenge presented in storing such procedures is that the nature of the object being stored can vary fundamentally with the actual instrument or instruments and experiment or experiments being performed. In particular, the presence or absence and ordering of entities in the XML document can represent the ordering of (and hierarchies in) the experimental procedure. Traditional static methods of mapping XML document entities into Java objects and/or relational database table columns are generally ill-equipped to handle such data, where mapping might require the explicit creation of a large number of storage instructions to account for an effectively infinite number of combinations of entities, and the ongoing addition of new instructions as new instrumentation is developed.

Traditional database management systems might attempt to address these problems by storing only the entire document (thereby, e.g., equating the database and the file system), but this, too, has disadvantages. For example, the XML documents (i.e., instrumentation procedures in this case) might not necessarily be readily identifiable through specific contained properties, thus passing responsibility for organizing the documents to client software (where, e.g., the client process may explicitly define storage of a procedure into a "project" or "computer"-specific repository, much like the process of choosing one disk folder over another for storage of a file). Laboratory data management system 100 addresses these problems by specifying a subset of the attributes from the instrumentation procedure to store explicitly.

Thus, FIG. 5A shows the root-level entities in the Impressionist procedure XML document, while FIG. 5B shows a portion of the fully expanded XML document including a portion of the definition of the experimental procedure. Those skilled in the art will note the heavy use of recursion in the procedure definition, which is common in laboratory control procedures.

Based on this XML document, database server process 130 defines a corresponding Java object whose fields are defined as follows:

```
public class Impressionist_Procedure_1 {
    public Long ID;
    public Long ConCheck;
    public String Name;
    public Boolean Enabled;
    public Long Version;
    public String Children;
    public String Author;
    public String Project;
    public Date CreationDate;
    public String Comments;
    public String UserFuncsAndSubs;
    public String Computer;
    public Boolean LoggingEnabled;
}
```

Database server process 130 maps this procedure to the table shown in FIG. 5C.

The XML document to Java class field mapping method described in the ReadXMLNode dicussion permits the explicit extraction and storage of the Name, Author, Project, CreationDate, Comments, Computer and LoggingEnabled aspects of an Impressionist procedure and the aggregation of the Children (and UserFuncsAndSubs) aspects of the Impressionist procedure into a single Java field and relational database table column. This permits the rapid organization of the database on explicit attributes and the flexibility of being able to store arbitrary procedure details.

FIGS. 6A–6D illustrate portions of an XML document representing data from an experiment on a Parallel Polymerization Reactor™ available from Symyx Technologies, Inc. of Santa Clara, Calif. FIG. 6A shows a portion the XML document representing the data from the Experiment base class from a PPR experiment (derived ClassName PPRExperiment), including a set of 17 experimental logs collected as part of the experimental run, represented within the Logs collection sub-entity of Experiment, with each Log being sub-object of the collection. FIG. 6B shows a portion of the same document with data from Log 713 expanded.

FIG. 6C shows the XML document for the PPRExperiment itself, including entities from the Experiment base class (with the Logs collection fully contracted), and several of the PPRElement objects that represent the data from the individual polymerization reactors. PPRElement 3456 is shown with all its data entities. In this implementation, PressureID, TemperatureID, ConversionID), PrePressureID, PreTemperatureID, and PreConversionID are data elements containing the ID number of XYDataSet objects, whose storage definition is discussed above. The TemperatureID, PressureID, PreTemperatureID, and PrePressureID XYDataSet objects are used to store the data traces from pressure and temperature sensors connected to the individual reactors on the device. The "Pre" designation is used to distinguish data collected before the catalyst is injected from data collected after injection. The ConversionID and PreConversionID XYDataSet objects represent the traces provided by a real-time calculation provided by the instrument software indicated the uptake of reactant gas in the reactor.

FIG. 6D again shows the entities from the Experiment base class, the PPRElements collection fully contracted, and the PPRModules collection with PPRModule 293 expanded to show the PPRReactor objects and their entities. In addition, this portion of the XML document describes the reactor configuration, here a combination of configurations for modules of 8 reactors, where some settings such as temperature, stir speed, and pressure transducer settings are module-based, and some such as reaction quenching, are reactor-based.

This XML document, recording an experiment of 48 reactors/PPRElements configured as 6 PPRModules of 8 PPRReactors each, contains 1,634,500 bytes of data, exclusive of the 288 XYDataSet objects used to store traces of pressure, temperature, and conversion data both pre- and post-catalyst injection for each reactor/PPRElement (48*3*2). The total size of the XML documents required to represent an average PPR Experiment is approximately 40 Mb.

The data from a PPRExperiment XML document is mapped to a number of Java objects: the base class Experiment, and its supporting sub-objects such as Keyword and Log; and the PPRExperiment itself, and its supporting sub-objects such as PPRElement, PPRModule and PPRReactor. Database server process 130 maps the data to Java classes as follows:

```
public class Experiment {
    public Long ID;
    public Date CreationDate;
    public String CreatedBy;
    public Date LastModificationDate;
    public String LastModifiedBy;
    public Long Status;
    public String ClassName;
    public String Comment;
    public String Project;
    public Long Notebook;
    public String Pages;
    public Long RootExperimentID;
    public Long LibDesignID;
    public Long Flags;
    public String Name;
```

```
    public Long Sequence;
    public OCollection Keywords;
    public OCollection Attachments;
    public Long ProtocolID;
    public Date StartDate;
    public Date EndDate;
    public OReference Equipment;
    public Long LibRows;
    public Long LibCols;
    public OCollection XMLAttachments;
    public Long ConCheck;
    public String Log;
    public String Barcode;
    public String Type;
    public Long LibID;
    public OCollection Logs;
    public String Staff;
}
public class Keyword {
    public Long ID;
    public String Value;
    public OReference Experiment;
    public Long ConCheck;
}
public class Log {
    public Long ID;
    public Long ConCheck;
    public OReference Experiment;
    public Date StartTime;
    public String Name;
    public String LogData;
    public String Procedure;
    public String Resources;
    public String Substrates;
    public String RecipeData;
}
public class PPRExperiment extends Symyx.Experiment {
    public OCollection PPRElements;
    public OCollection PPRModules;
    public String StartupProc;
    public String ShutdownProc;
    public String Notes;
}
public class PPRElement {
    public Long ID;
    public Long ConCheck;
    public Long Position;
    public Long Flags;
    public Long Status;
    public Long PressureID;
    public Long TemperatureID;
    public Long ConversionID;
    public Double FinalConversion;
    public Double FinalPressure;
    public Double FinalTemperature;
    public Long PreTemperatureID;
    public Long PreConversionID;
    public Long PrePressureID;
    public OReference Experiment;
    public Long LibID;
    public Long LibPosition;
}
public class PPRModule {
    public Long ID;
    public Long ConCheck;
    public OReference PPRExperiment;
    public Long LibID;
    public Double Temperature;
    public Double TemperatureDeadband;
    public Double MaxTemperature;
    public Double StirSpeed;
    public Double Pressure;
```

```
        public Double PressureDeadband;
        public Double MaxReactionTime;
        public Boolean Enabled;
        public OCollection PPRReactors;
    }
    public class PPRReactor {
        public Long ID;
        public Long ConCheck;
        public String QuenchMode;
        public Double QuenchValue;
        public OReference PPRModule;
    }
```

Database server process 130 maps these classes to tables defined by the entity-relationship diagram as shown in FIG. 6E.

Database server process 130 retrieves data from database 180 using a method public String GetObject2(String objName, long ID, Boolean InclueBinaryData, Boolean UseBLOBFiles), exemplified in code Listing 2, below.

This method accepts a string containing the name of the object to be retrieved, the ID number of the object, and 2 Boolean parameters that control retrieval of binary data.

The overall process is the reverse of the process of storing objects: retrieve the object by ID from the database and create a Java object by name and populate its fields (and sub-objects as necessary). This Java object is then mapped into an XML document and the document is returned to the requester as a string using the WriteXMLNode method.

Client processes 140 (and users of those processes) see only the object representation of the underlying data and can interact with that data only through database server 130. In one implementation, client processes 140 interact with the underlying data through a proxy object server, such as a COM dll, configured to receive an XML representation of data from database server process 130 and construct a set of interfaces (consistent, e.g., with Microsoft's COM standard or the CORBA standard) that present a set of methods and properties representing a particular object or objects. Alternatively, client processes 140 can interact with the data directly through the XML representation—for example, by processing the XML document using a set of XSLT transformation rules to generate an HTML document which is then presented to the user in a Web browser as an Experiment write-up document. Because clients and users are isolated from the details of data storage in database 180, they can only manipulate data in ways explicitly permitted by database server process 130, which restricts their ability to retrieve or alter data without authorization.

Client processes 140 can also evolve separately from the database 180. Thus, for example, if a client process 140 generating a new form of data (e.g., a "new" type of experiment for which no derived class has been defined in system 100) is added to system 100 (or if an existing client process 140 is modified to generate a new form of data), the client process can simply embed the new data into the XML data stream sent to database server process 130, e.g., as an entity describing Experiment object (an instance of the Experiment base class) having a classname property identifying the new experiment type.

Database server process 130 can be configured to map any new form of data (i.e., data that is not explicitly encompassed in the middle tier mapping schema) to default storage such as an "unknowns" column in database 180. Database 180 can be modified at a later date to handle this data explicitly. Alternatively, database server process 130 can be configured to generate an error message when it encounters an unrecognized form of data, notifying a database administrator of the presence of unrecognized data and providing a detailed explanation of the error (in the form of the XML stream) to enable the administrator to diagnose and fix the problem. Thus in the case of a "new experiment type" discussed above, upon encountering an unrecognized classname database server process 130 can be configured to create an instance of the Experiment base class describing the general characteristics of the experiment as discussed above, and to store the as-yet-unrecognized experimental detail embodied in the particular derived properties in generic storage, for later explicit treatment by a system administrator or the like. Alternatively, database server process 130 can be configured to generate new derived Experiment classes dynamically, using information contained within the XML representation as a framework for identifying and populating object properties, and/or mapping such properties to new or existing tables in database 180.

A method 700 of using system 100 to retrieve data from database 180 is illustrated in FIGS. 7 and 8A–B. The method begins in step 710, where, for example, the user selects File>New Query from a menu bar in a Queries window displayed by user interface program 160. Optionally, system 100 prompts the user to select a project or projects to search (step 720)—e.g., from a drop down list of projects defined in database 180. In response, system 100 establishes a workflow for searching stored data for the specified project or projects (step 730). The user can search by queryable fields defined for the specified projects, which may include, for example, library ID number, experiment number, experiment name, status, keyword or the like. The user can also search by particular types of experiments defined for the specified projects—for example, GPC Experiments for a gel permeation chromatography project or Synthesis Protocols for library synthesis. For each type of experiment, the user can select from project-specific fields defined in metadata for the experiment type—for example, GPC retention time, average polydispersity index, or the like for the gel permeation chromatography experiment referenced above.

The user formulates a query by specifying a search domain (all experiments, experiment types, library elements, etc.) using, e.g., radio buttons 800 and/or drop down list 805 (step 740), selecting one or more search fields and a comparison operator in drop down lists 810 and 815, and specifying a value to search against in Value box 820 (step 750). The user can specify additional search terms by selecting an appropriate connector (e.g., and, or) in Combine box 825, in response to which system 100 causes user interface program 160 to display an additional row 830. Optionally, user interface program 160 is configured to indicate an incomplete or invalid query by identifying fields requiring specification by, for example, outlining or coloring the necessary fields in red.

System 100 can represent queries as objects, XML strings and entries in relational tables in database 180. Queries are formulated as objects in user interface program 160. In response to a request to save or execute a search, user interface program 160 generates an XML string corresponding to the query object, which it transmits to database server process 130. Database server process 130 parses the XML stream and, to save the query in database 180, maps entities extracted from the XML stream to appropriate database tables as described above. The user can retrieve a saved query from database 180 by selecting a query from a list 840 of available queries previously stored in database 180, which may also identify, e.g., queries previously created during a particular session. Queries can also be exported to files for storage.

The user runs the search by, e.g., selecting an appropriate menu item or button. User interface program 160 generates the appropriate XML string, which it sends to database server process 130 (step 760). Database server process 130 parses the data stream and generates appropriate commands in a data definition and/or manipulation language such as SQL, which it uses to search for responsive records in database 180 (step 770). Database server process 130 searches the appropriate tables in database 180 for any record that satisfies the specified search terms, and assembles the results into the form of a list object (step 780). The list object can subsequently be used by user interface program 160 to, for example, present the number of hits returned by the user's query, and it can be independently stored in database 180 for sharing with other users or for later use. Using the list, user interface program 160 requests a tabular representation of the object data for those objects on the list. The tabular representation capability of the server provides access to data for multiple objects in a compact form resembling a single relational table, and is useful for producing reports including selected data from many different objects or in presenting a list of objects from which the user might select one or more for full expansion. Furthermore, the tabular representation may be a more efficient means of retrieving data from a large number of objects as opposed to retrieving each object via the XML document representation since it accomplishes the retrieval for all objects in a single operation and the data is "flattened" into a single table. However, the data available in the tabular representation may not include all the object data—specifically, it cannot be used to retrieve data from sub-objects or collections of sub-objects, since it is by definition a single table with each row representing a single object. For this reason, database server process 130 can also be configured to return results in an object form (e.g., as an XML stream), and clients 140 can be configured to operate on data using both the object-XML representation for access to all object data and the tabular representation for access to data for a larger number of objects. In one implementation, the tabular representation may take the form of a Microsoft Active Data Object (ADO) Recordset object, where the data from the server is returned to the user interface client as an ADO Recordset object. Database server process 130 returns the search result for display by user interface program 160 or use by other client process 140 (step 790).

As discussed above, in one implementation database server process 130 formats the recordset as a list of elements that satisfy the terms of the query. Lists can be stored in database 180 and can be exported to files for storage. To store a list in database 180, the user selects File>Save List from a menu and selects the desired list from a set of available lists 850 (including, e.g., one or more lists generated by the user during a particular session). Optionally, user interface program 160 can prompt the user for list metadata, such as a flag indicating that the list should be public (i.e., made available to other users of system 100) or private, or a project name and/or description to be associated with the stored list. In one implementation, stored lists are static (i.e., database server process 130 does not update the list to include query-satisfying records added to database 180 after the underlying query was saved), while database server process 130 updates the data content of records included in a stored list when the list is retrieved from database 180 or opened by user interface program 160.

The user views a list by selecting the desired list from a set of available lists identified in Available Lists pane 850. Optionally, user interface program 160 provides a preview pane 860 showing list data for a current list—including, for example, columns corresponding to an element ID for each element satisfying the respective query terms, a library ID for the library containing the element, an experiment number, a position for the element in the library, any flags set for the library, a library status, and experimental data such as average molecular weight.

The user views data for a selected list by creating a Report (e.g., by selecting a menu item Report>Create Report). User interface program 160 and database server process 130 are configured to report experimental data in one or more formatted reports, such as spreadsheets, 2D or 3D plots, bubble plots, data grids and other known display formats. Optionally, database server process 130 can export record-sets for use in commercially available software application programs such as Spotfire, available from Spotfire, Inc. of Cambridge, Mass.

As shown in FIG. 9A, a spreadsheet 900 displays data for one or more selected fields for each element in a list. The user selects fields to display in a spreadsheet by, e.g., selecting the desired fields in a tree display 910 of available fields shown in FIG. 9B, which can include one or more displayable fields defined for the search domain specified as described above, such as average Mw, Mn, and PDI, data status or category, library ID, experiment ID or the like as shown in FIG. 9B. Displayable fields can also include images and data graphs, such as in chromatogram column 905 in FIG. 9A. System 100 generates a spreadsheet 900 having one or more rows corresponding to the elements satisfying the query, and one or more columns corresponding to the selected displayable fields.

The displayed fields can, but need not necessarily, correspond to the queryable fields on which the database query was based, as described above. Rather, while formatting the data for display the user can select displayable fields in addition to or instead of the queryable fields used to construct the query that retrieved the data in the first instance. In addition to adding and removing displayable field columns from spreadsheet 900, the user can change the format of spreadsheet 900 by, e.g., changing fonts, column widths, data alignment and the like. The user can also merge field data that does not change across rows into single rows, move rows or columns in the spreadsheet, set minimum and maximum values for x and y coordinates of data graphs, and assign a status value to a row or rows in the spreadsheet. If database 180 includes multiple values for a particular field or fields for a given library element (e.g., values for multiple instances of a particular experiment performed on a particular library or library element), the user can choose to view all such values, or can choose to view the minimum, maximum, or average of the stored values, or the first or most recent values stored in database 180.

Similarly, the user can view the data as a two-dimensional plot, three dimensional plot or bubble plot, as shown in FIGS. 9C, 9D and 9E. Likewise, the user can also view data in the form of a data grid displaying experimental data (including graphs) as a grid of values for the rows and columns of each experiment (i.e., each library) in a selected list.

A number of embodiments of the invention have been described. Nevertheless, it will be understood that various modifications may be made without departing from the spirit and scope of the invention. Accordingly, other embodiments are within the scope of the following claims.

Listing 1.

```
/**
 * Store an object in the databas .
 * @param xml XML stream representation of the object.
 * @return the ID of the object stored (>= 2) or en error;
 * 0        general error
 * -1       unable to retrieve new object ID
 * -2       update conflict: ConCheck value in the database is not the same as the
            incoming abject's
 * -3       invalid class
 * -4       mapping error
 * -5       database error (including db integrity check failure)
 * -6       exception in inner object save
 * -7       XML/obj schema mismatch: unknown object or attribute name
 * -8       userID not provided or not authenticated
 * -9       internal error
 */
public long Save(String.xml)
{
    Log.setFile("Save");
    if (_logLevel > 1)
        Log.Log("U2", "Entering Save", 0);
    try
    {
        // parse the XML
        clientutilities.XMLHelper helper = new clientutilities.XMLHelper( );
        clientutilities.IXMLEntity docNode = helper.LoadDocument(xml);
        return SaveXML(docNode);
    }
    catch (Exception ignore)
    {
        Log.Log("E", "Unable to load XML document", 1181);
    }
    finally
    {
        if (_logLevel > 1)
            Log.Log ("U2", "Exiting save" 0);
    }
    return -9;
}
private long SaveXML(clientutilities.IXMLEntity docNode)
{
    Log.setFile("SaveXML");
    if (_logLevel > 1)
        Log.Log("U2", "Entering SaveXML", 0);
    long retCode = 0;
    try
    {
        // parse the XML
        clientutilities.IXMLEntity rootNode =]docNode.FirstChild( );
        // extract root node name, make into database object
        boolean existingObject = false;
        Object rootObj = XMLNodeToObject(rootNode);
        if (rootObj == null)
        {
            Log.Log("E", "Conflict in concurrency check value updating " +
            rootNode.getEntityName( ), 807);
            return -2;
        }
        // get relevant object-level attributes
        if
            (((Long)(rootObj.getClass( ).getField("ConCheck").get(rootObj))).longValue(
            ) > 0)
            existingObject = true;
        else
            existingObject = false;
        int persistState rootNode.GetLongAttribute("PersistState");
        // validate user and lock this session
        String userID = rootNode.GetStringAttribute ("UserID");
        if (userID == null)
        {
            Log.Log("E", "No userID to update " + rootNode.getEntityName( ), 1517);
            returo -8;
        }
```

-continued

Listing 1.

```
        // map each XML entity under the root into a field
        clientutilities.IXMLEntity node = rootNode.FirstChild( );
        while (node != null)
        {
            retCode = ReadXMLCode(node, rootObj, userID);
            if (retCode < 0)
            {
                Log.Log("W", "Update( ) unable to read XML node: " +
                    node.getEntityName( ) + " of root entity " + rootNode.getEntityName( )
                    + " for user " + userID, 668);
                return retCode;
            }
            else if (retCode > 0)
            {
                // update the root object persist state based on sub-object processing
                persistState = (int)retCode;
            }
            node = node.NextSibling( );
        }
        // see if the root object has a "ClassName" field- if so, populate it with
            the class name
        try
        {
            Field typeFld = rootObj.getClass( ).getField("ClassName");
            if (typeFld != null)
            {
                String typeName =
                    ObjectNameFromClassName(rootObj.getClass( ).getName( );
                typeFld.set(rootObj, typeName);
            }
        }
        catch (Exception ignore)
        {
        }
        // update a root object
        long newID = SaveObject (rootObj, userID, persistState);
        Log.Log("U1", "Saved " + rootNode.getEntityName( ) + " ID =p0 " + newID, 0);
        rootObj = null;
        return newID;
    }
    catch (Exception e)
    {
        Log.Log("E", "Exception: " + e.toString( ), 738);
        return 0;
    }
    finally
    {
        // unlock session before returning
        AurthorizeUser("");
        if (_logLevel > 1)
            Log.Log("U2", "Exiting SaveXML", 0);
    }
}
// return < 0 error code, > 0 subobject persist state change
private long ReadXMLMode(clientutilities.IXMLEntity node, java.lang.Object obj,
String UserID)
{
    Log.setFile("ReadXMLNode");
    try
    {
        if (node != null)
        {
            String nodeName = node.getEntityName( );
            Class objCls = obj.GetClass( );
            clientutilities.IXMLEntity subNode = node.FirstChild( );
            //delete the object
            if (node.GetLongAttribute("PersistState") == StateFlag.stateDeleted)
            {
                _db.delete(obj);
                return StateFlag.stateDeleted;
            }
            // delete the data (different from deleting the object!)
            else if (node.GetLongAttribute("Null") == 1)
            {
```

-continued

Listing 1.

```
        Field fld = objCls.getField(nodeName);
        fld.set(obj, null);
        _db.markUpdate(obj);
}
// BLOB data nodes
else if (node.GetStringAttribute("File") != null)
{
        Field fld = objCls.getField(nodeName);
        java.lang.Object oVal = EntityToFieldObjectValue(node, fld);
        fld.set(obj, oVal);
}
// otherwise we're updating or inserting
// skip entirely empty collection nodes
else if (subNode != null)
{
        String subnodeName = subNode.getEntityName( );
        // leaf nodes have data to extract
        if (subnodeName.equalsIgnoreCase("#text"))
        {
                Field fld = objCls.getField(nodeName);
                java.lang.Object oVal = EntityToFieldObjectValue(node, fld);
                fld.set(obj, oVal);
        }
        // subparents have references/collections to extract recursively
        // subparent object reference- subnodes or the subparent have values:
        // <node><B>#text</B></node>
        // subparent object collection: subnodes of the subparent de not have
                data:
        // <node><subnode><G>#text</B></subnode></node>
        else
                // get the field from the object
                Field collFld = objCls.getField(nodeName);
                // if we have a string field, then store the entire XML node stream
                        as a value
                if (collFld.getType( ).getName( ).equalsIgnoreCase("java.lang.String"))
                {
                        // 09-05-00 DD fix to store node XML, not subnode!
                        java.lang.String nodeXML = "<?xml version='1.0' ?>" +
                        node.GetXML(false);
                        collFld.set(obj, nodeXML);
                }
                else
                {
                        // get the actual field instance (NOT the definition)
                        Object collObj = collFld.get(obj);
                        String fldType = collObj.getClass( ).getName( );
                        // collection attributes
                        if (fldType.equalsIgoreCase("com.objectmatter.bsf.OCollection"))
                        {
                                // try to create (or retrieve) the first subobject from the
                                        collection
                                com.objectmatter.bsf.OCollection collData =
                                (com.objectmatter.bsf.OCollection)(collObj);
                                Object subObj = XMLNodeToCollectionObject(collData, subNode);
                                boolean existingObject = false;
                                // otherwise loop over all subNode (objects)
                                while (subNode != null)
                                {
                                        // existing or new?
                                        if
                                                (((Long)(subObj.getClass( ).getField("ComCheck").get(subObj))).1
                                                ongValue( ) > 0)
                                                existingobject = true;
                                        else
                                                existingObject = false;
```

-continued

Listing 1.

```
            // delete the object
            if (subNode.GetLongAttribute("PersistState") ==
                StateFlag.stateDeleted)
            {
                __db.delete(subObj);
            }
            // or insert/update
            else
            {
                // loop over all attribute values
                clientutilities.IXMLEntity subsubNode = subNode.FirstChild( );
                while (subsubNode != null)
                {
                    String subsubNodeName = subsubNode.getEntityName( );
                    long retCode = ReadXMLNode(subsubNode, subObj, UserID);
                    // return immediate error
                    if (retCode < 0)
                    {
                        Log.Log("E", "Unable to read subNode " + subsubNodeName,
                            885);
                        return retCode;
                    }
                    subsubNode = subsubNode.Nextsibling( );
                }
                if (existingobject == true)
                    __db.markUpdate (subObj);
                else
                    collData.add(subObj);
            }
            // get next another subobject
            subNode = subNode.NextSibling( );
            if (subNode != null)
                subObj = XMLNodeToCollectionObject(collData, subNode);
        }
    }
// this entity maps to a referenced object: 'node' is a subobject
        and the
else if
        (fldType.equalsIgnoreCase("com.objectmatter.bsf.OReference"))
{
    com.object.matter.bsf.OReference refObj =
        (com.objectmatter.bsf.OReference)collObj;
    boolean existingObject = false;
    // create (or retrieve) the object
    Object subObj = null;
    try
    {
        // get node name and try to make a database object
        com.objectmatter.bsf.mapping.schema.ClassSchema schema =
            __db.getClassSchema(obj.getClass( ):getName( ));
        String objName =
            schema.getAttribute(nodeName).getRefClassName( );
        long ID = node.GetLongAttribute("ID");
        // this is an update (existing object)
        if (ID > 0)
        {
            subObj = __db.lookup(objName, ID);
            // did not find object in database. use ID and insert
            if (subObj == null)
            {
                subObj =__db.create(objName);
                Field fld = subObj.getClass( ).getField("ID");
                fld.set(subObj, new Long(ID));
                fld = subObj.getClass( ).getField("ConCheck");
                fld.set(subObj, new Long(0));
            }
            // If found object-ID in database, do a version check
            else
            {
                Class subObjCls = subObj.getClass( );
            // check concurrency value of XML against the database
            long conValue = node.GetLongAttribute("ConCheck");
            long dbConValue =
            ((Long)(subObjCls.getField("ConCheck").get(subObj))).longVa
            lue( );
            if (conValue != dbConValue)
            {
```

Listing 1.

```java
                Log.Log("E", "Conflict in concurrency check value
            updating " + node.getEntityName( ), 1721);
                return -2;
            }
            existingObjeot = true;
        }
    }
    // this is an insert (new object)
    else
    {
        subObj = __db.create(objName);
        Field fld = subObj.getClass( ).getField("ID");
        String newID =
            AllocatObjectID(ObjectNameFromClassName(objName));
        fld.set(subObj, new Long (newID));
        fld = subObj.getClass( ).getField("ConCheck");
        fld.set(subObj, new Long(0));
        existingObject = false;
    }
}
catch (Exception e)
{
    Log.Log("E", "Unable to create subobject " + nodeName, 1742);
    return -7;
}
if (subObj != null)
{
    int persistState = node.GetLongAttribute ("PersistState");
    // loop over all subobject values (attributes)
    while (subNode != null)
    {
        long retCode = ReadXMLNode (subNode, subobj, UserID);
        if (retCode < 0)
            return retCode;
        subNode = subNode.NextSibling( );
    }
    // if the referenced object is not owned, then update it if it
        doesn't have an ID already
    // in this case, the referenced object MUST be a root object
        in terms of attributes!
    if
        (__db.getClassSchema(obj.getClass( ).getName( )).getAttribute(no
        deName).isOwnership( ) == false &&
        refObj.isContained( ) == false)
    {
        if (AnthorizeUser(UserID) == false)
        {
            Log.Log("E", "Unauthorised user updating " +
            subObj.getClass( ).getName( ), 827);
            return -8;
        }
        // update a root object
                long subObjID = UpdateRootObject(subObj, existingObject,
                persistState);
                if (subObjID < 0) return subObjID;
                // add a reference to this object to the collection if not
                existing
                // the actual field instance (NOT the definition)
                com.objectmatter.bsf.OReference refData =
                    (com.objectmatter.bsf.OReference)(objCls.getField(nodeName
                    ).get(obj));
                refData.set(subObj);
        }
    }
    // if the object wasn't able to be created. try and see if we
        have a field in which to store the
    // entire subobj as a value
    else
    {
        // only if this is a string field!
        collFld = objCls.getField(nodeName);
        if (collFld != null &&
                collFld.getType( ).getName( ).equalsIgnoreCase("java.lang.Str
                ing"))
        {
            java.lang.string subnodeXML =node.GetXML(false);
            collFld.set(obj, subnodeXML);
```

Listing 1.

```
                                    }
                                    else
                                    {
                                        // not able to map an XML entity to any object attribute.
                                        Log.Log("E", "Unable to map " + nodeName + " entity to
                                            attribute or subject ", 1793);
                                        return −7;
                                    }
                                }
                            }
                        }
                    }
                }
            }
            return StateFlag.stateChanged;
        }
        catch (Exception e)
        {
            Log.Log("E", "Exception: " + e.toString( ), 933);
        }
        finally
        {
            // clear userID (from any subobject inserts)
            AuthorizeUser ("");
        }
        return −6;
}
private java.lang.Oject EntityToFieldObjectValue(clientutilities.IXMLEntity
node, java.lang.reflect.Field fld)
{
    if (node == null || fld == null)
        return null;
    try
    {
String fldType = fld.getType( ).getName( );
if (fldType.equalsIgnoreCase("java.lang.Boolean"))
{
        if (node.getLongValue( ) == 0)
            return new java.lang.Boolean(fals );
        else
            return new java.lang.Boolean(true);
}
else if (fldType.equalsIgnoreCase("java.lang.Double"))
{
    return new java.lang.Double(node.getDoubleValue( ));
}
else if (fldType.equalsIgnoreCase("java.lang.Long"))
{
    return new java.lang.Long(node.getLongValue( ));
}
else if (fldType.equalsIgnoreCase("java.lang.String"))
{
    return new java.lang.String(node.getStringValue( ));
}
else if (fldType.equalsIgnoreCase("java.util.Date"))
{
    return new jeva.util.Date(node.getStringValue( ));
}
else if (fldType.equalsIgoreCase("[B"))
{
    String fileName = node.GetStringAttribute("File"), msg;
    com.ms.com.SafeArray sa = null;
    if (fileName != null && fileName.length( ) > 0)
    {
        clientutilities.FileHelper fh = new clientutilities.FileHelper( );
        com.ms.com.Variant var = fh.ReadFile(fileName, FileType.fileBinary);
        if (var.getvt( ) == com.ms.cma.Variant.VariantArray +
                com.ms.com.Variant.VariantByte)
        {
            sa = var.toSafeArray( );
            msg = "BLOB read from file";
        }
        else
        {
            msg = "Unable to read BLOB from file";
        }
    }
```

| Listing 1. |
| --- |

```
        else
        {
            sa = node.getBinaryValue(com.ms.com.Variant.VariantByte);
            msg = "BLOB read from XML stream";
        }
        if (sa.getvt ( ) == com.ms.oom.Variant.VariantByte)
        {
            int nelems = sa.getUBound( ) – sa.getLBound( ) + 1;
            if (_logLevel > 1)
                Log.Log("U1", msg + ", size " + nelems, 989);
            byte [ ] ba = new byte(nelems);
            sa.getBytes(0, nelems, ba, 0);
            if (fileName != null && fileName.length( ) > 0)
            {
                java.io.File f = new java.io.File(fileName);
                f.delete( );
            }
            return ba;
        }
    }
        else
        {
            Log.Log ("W", "Unmappable field type " + fldType, 1015);
        }
}
catch (Exception e)
{
    Log.Log("E", "Exception: " + e.toString( ), 1009);
}
return null
        }
```

| Listing 2 |
| --- |

```
/**
* Retrieve a single object in XML form from the database.
* @param objName of the object
* @param ID ID of the obj ct
* @param IncludeBinaryData True to include binary in the returned
  objects, False to include
* data only from non-BLOB atttributes
* @param UseBLOBFiles True to transfer BLOB data through a file share,
  False to include the BLOB data
* in the XML stream (only used if IncludeBinary Data is True)
* @return XML stream containing the object attribute data, empty string
  if an error occurs
*/
public java.lang.String GetObject2(String objName, long ID, boolean
IncludeBinaryData, boolean UseBLOBFiles)
{
    Log.setFile("GetObject2");
    if (_logLevel > 1)
        Log.Log("U3", "Entering GetObject2". 0);
    if (_db == null) return "";
    try
    {
        String clsName = ClassNameFromObjectName(objName);
        Class objCls = Class.forName(clsName);
        if (objCls = null)
        {
            Log.Log("W", "No known object: " + clsName, 567);
            return "";
        }
        if (_logLevel > 1)
            Log.Log("U3", "Object " + clsName + ", ID = " + ID + " retrieve",
                0);
        java.lang.Object obj = _db.lookup(objCls, ID);
        if (obj == null)
        {
            Log.Log("W", "Object not found: " + clsName + ", ID = " + ID, 573);
            return "";
        {
```

-continued

Listing 2

```
            objCls = obj.getClass( );
            if (_logLevel > 1)
                Log.Log("U3", "Object " + clsName + ", ID = "+ ID + " found", 0);
            // make it into XML
            clientutilities.XMLHelper helper == new clientutilities.XMLHelper( );
            if (helper == null)
            {
                Log.Log("E", "Unable to create XMLHelper instance". 582);
                return "";
            }
            clientutilities.IXMLEntity docNode = helper.CreateDocument("", "");
            clientutilities.IXMLEntity rootNode = docNode.AddEntity(objName);
            if (rootNode == null)
            {
                Log.Log("E", "Unable to create XML document", 590);
                return "";
            }
            WriteXMLnode(rootNode, obj, IncludeBinaryData, UseBLOBFiles);
            if (_logLevel > 1)
                Log.Log("U3", "Obj ct " + clsName + ", ID = " + ID + "XML object
                    prepared", 0);
            String xml = rootNode.GetXML(tru );
            if (_logLevel > 1)
            {
                Log.Log("U3", "Object " + clsName + ", ID = " +ID + " XML stream
                    complete", 0);
                Log.Log("U1", "GetObject2 returned " + objName + " " + ID, 0);
            }
            // update counter
            com.ms.wfc.app.RegistryKey regKey =
                com.ms.wfc.app.Registry.LOCAL_MACHINE.getSubKey("Software\\Symyx
                Technologies\\SymyxDb", false);
            if (regKey != null)
            }
                Long tot = new Long( ((String)regKey.getValue("ObjectsReturned")) );
                long total = tot.longVaLue( ) + 1;
                regKey.setValue("ObjectsReturned", new Long(total).toString ( ));
                regKey.close( );
            }
            return xml;
        }
        catch (BODBException e)
        {
            Log.Log("E", "BODBException: " + e.toString( ), 600);
            return "";
        }
        catch (Exception e)
        {
            Log.Log("E", Exception: " + e.toString( ), 605);
            return "";
        }
        finally
        {
            if (_logLevel > 1)
                Log.Log("U3", "Exiting GetObject2", 0);
        }
    }
}
// used to keep list of current parents during recursive processing
private static java.util.Stack parentNodeList = new java.util.Stack( );
private boolean WriteXMLNode(clientutilities.IXMLEntity node,
java.lang.Object obj, boolean IncludeAttachments, boolean UseBLOBFiles)
{
    Log.setFile("WriteXMLNode");
    try
    {
        Field fld;
        Class objCls = obj.getClass( );
        // track objects by object class Name and hashcode
        parentNodeList.addElement(obj.toString( ));
        // node attributes
        fld = objCls.getField("ID");
        node.AddLongAttribute("ID", ((Long)fld.get(obj)).intValue( ));
        fld = objCls.getField("ConCheck");
        node.AddLongAttribute("ConCheck", ((Long)fld.get(obj)).intValue( ));
        nods.AddLongAttribute("PersistState", StateFlag.stateSaved);
        // now write public entity field values
        Field flds[ ]= objCls.getFieids( );
```

Listing 2

```
            for (int i = 0; i < flds.length; ++i)
{
    fld = flds[i];
    if (Modifier.isPublic(fld.getModifiers( )))
    {
        String fldName = fld.g tName( );
        if (fldName.equalsIgnoreCas ("ID") == false &&
                fldNam .equalsIgnoreCase("ConCheck") == false)
        {
            String fldType = fld.getType( ).getName( );
            if
                (fldType.equalsIgnoreCase("com.objectmatter.bsf.OCollection")
                )
            {
                Object[ ] val = ((OCollection)fld.get(obj)).get( );
                if (val != null)
                {
                    // create the overlying entity
                    clientutilities.IXMLEntity subMods =
                            node.AddEntity(fldName);
                    // write each subentity
                    for (int j = 0; j < val.length; ++j)
                    {
                        Object ele = val [j];
                        String eleName =
                        ObjectNameFromClassName(ele.getClass( ).getName( ));
                        clientutilities.IXMLEntity eleNode =
                        subNode.AddEntity(eleName);
                        WriteXMLNode(eleNode, ele. IncludeAttachments,
                        UseBLOBFiles);
                    }
                }
            }
            else if
                (fldType.equalsIgnoreCase("com.objectmatter.bsf.OReference"))
            {
                // only write child references, not parents
                com.objectmatter.bsf.OReference refVal =
                (com.objectmatter.bsf.OReference)fld.get(obj);
                Object val = retVal.get( );
                if (val != null && parentNodeList.contain(val.toString( )) ==
                        false)
                {
                    clientutilities.XMLEntity subNode =
                            node.AddEntity(fldName);
                    // need to pop this object off the parent list to write it
                    //parentNodeList.removeElement(obj.toString( ));
                    WriteXMLNode(subNode, val, IncludeAttachments,
                            UseBLOBFiles);
                }
            }
            else if (fldType.equalsIgnoreCase("java.lang.Boolean"))
            {
                Object val = fld.get(obj);
                if (val != null)
                {
                    clientutilities.IXMLEntity eleNode =
                            node.AddEntity(fldName);
                    if (((Boolean)(val)).booleanValue( ) == true)
                        eleNode.setLongValue(-1);
                    else
                        eleNode.setLongValue(0);
                }
            }
            else if (fldType.equalsIgnoreCase("java.lang.Double"))
            {
                Object val = fld.get(obj);
                if (val != null)
                {
                    clientutilities.IXMLEntity eleNode =
                            node.AddEntity(fldName);
                    eleNode.setDoubleValue((Double)(val)).doubleValue( ));
                }
            }
            else if (fldType.equalsIgnoreCase("java.lang.Long"))
            {
                Object val = fld.get(obj);
```

Listing 2 (-continued)

```
            if (val != null)
            {
                clientutilities.IXMLEntity eleNode =
                    node.AddEntity(fldName);
                eleNode.setLongValue(((long)(val)).intValue( ));
            }
        }
        else if (fldType.equalsIgnoreCase("java.lang.String"))
        {
            Object val = fld.get(obj);
            if (val != null)
            {
                String sVal = (String)val;
                // value is to be intrepreted as in-line XML
                if (sVal.startsWith("<?xml") == true)
                {
                    clientutilities.XMLHelper helper = new
                        clientutilities.XMLHelper( );
                    clientutilities.IXMLEntity rootNode =
                        helper.LoadDocument(sVal);
                    // if it was xml, then add a (parsed) subnode
                    if (rootNode != null)
                    {
                        node.AddSubnode(rootNode.GetEntity(fldName));
                    }
                    // otherwise the XML (string) is invalid...add a subnode
                        and stick in a string
                    else
                    {
                        clientutilities.IXMLEntity eleNode =
                        Node.AddEntity(fldName);
                        eleNode.setStringValue((String)val);
                    }
                }
                // value is textual
                else
                {
                    clientutilities.IXMLEntity eleNode =
                        node.AddEntity(fldName);
                    eleNode.setStringValue((String)val);
                }
            }
        }
        else if (fldType.equalsIgnoreCase("java.util.Date"))
        {
            Object val = fld.get(obj);
            if (val != null)
            {
                clientutilities.IXMLEntity eleNode =
                    node.AddEntity(fldName);
                OleDate od = new OleDate((java.util.Date)val);
                eleNode.setDateValue(od.toDoubie( ));
            }
        }
        else if (fldType.equalsIgnoreCase("8 B"))
        {
            if (IncludeAttachments == true)
            {
                Object val = fld.get(obj);
                if (val != null)
                {
                    byte [ ] ba = (byte [ ])val;
                    int nelem = ba.length;
                    if (nelem > 0)
                    {
                        clientutilities.IXMLEntity eleNode =
                            node.AddEntity(fldName);
                        com.ms.com.SafeArray sa = new
                            com.ms.com.SafeArray(com.ms.com.Variant.VariantByte
                            , nelem);
                        sa.fromByteArray(ba);
                        com.ms.com.Variant va = new com.ms.com.Variant( );
                        va.putSafeArray(sa);
                        if (UseBLOBFiles == false || nelem < _minBLOBFilesSize)
                        {
                            eleNode.setValue(va);
                            if (_logLevel > 1)
```

-continued

Listing 2

```
                        Log.Log("U1", "BLOB written to XML stream, size " +
                            nelem, 1335);
                }
                else
                {
                        clientutilities.FileHelper fh = new
                            clientutilities.FileHelper( );
                        if (fh != null)
                        {
                            String fName = fh.GetUniqueFilename (_BLOBFilePath,
                                "BLB");
                            fh.WriteFile (fName, va);
                            eleNode.AddStringAttribute("File", fName);
                            if (_logLevel > 1)
                                Log.Log("U1", "BLOB written to file, size " +
                                    nelem, 1345);
                        }
                    }
                }
            }
        }
        else
        {
            Log.Log("W", "Unmappable field type " + fldType, 1398);
        }
      }
    }
  }
  // remove this parent from the processing stack
  parentNodeList.removeElement(obj.toString( ));
  return true;
}
catch (Exception e)
{
  Log.Log("E", "Exception: " + e.toString( ), 1184);
}
  return false;
}
```

What is claimed is:

1. A computer-implemented method for processing data from a chemical experiment on a library of materials, the method comprising:

receiving data from a chemical experiment on a library of materials having a plurality of members;

associating the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials;

parsing the representation to map data from the representation to one or more tables in a relational database; and storing the data from the representation in the relational database according to the mapping.

2. The method of claim 1, wherein:

parsing the representation includes extracting object information from the representation, and mapping one or more object properties to one or more database tables based on the extracted object information.

3. The method of claim 2, wherein:

the extracted object information includes for each object in the representation an object class and one or more object properties; and parsing the representation includes mapping different classes of objects to different database tables, with each row in a given database table representing an object instantiated from the corresponding class and each column corresponding to one of a set of properties defined for objects instantiated from the class.

4. The method of claim 1, wherein:

the chemical experiment has an experiment type corresponding to one of a set of one or more experiment types;

the chemical experiment is represented by a generic experiment object and a derived experiment object, the generic experiment object having a classname property and a library ID property, the classname property associated with the experiment type of the chemical experiment and the library ID property identifying the library of materials, the derived experiment object having a plurality of derived experiment class properties derived from the associated experiment type; and parsing the representation includes mapping the generic experiment object to a database table including data for experiments having a plurality of different experiment types in the set of experiment types arid mapping the derived experiment object to a database table including data only for experiments having the experiment type of the chemical experiment.

5. A computer program product on a computer-readable medium for processing data from a chemical experiment on a library of materials, the computer program product comprising instructions operable to cause a programmable processor to:

receive data from a chemical experiment on a library of materials having a plurality of members;

associate the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials;

parse the representation to map data from the representation to one or more tables in a relational database; and store the data from the representation in the relational database according to the mapping.

6. The computer program product of claim 5, wherein:

the instructions operable to cause a programmable processor to parse the representation include instructions operable to cause a programmable processor to extract object information from the representation and map one or more object properties to one or more database tables based on the extracted object information.

7. The computer program product of claim 6, wherein:

the extracted object information includes for each object in the representation an object class and one or more object properties; and the instructions operable to cause a programmable processor to parse the representation include instructions operable to cause a programmable processor to map different classes of objects to different database tables, with each row in a given database table representing an object instantiated from the corresponding class and each column corresponding to one of a set of properties defined for objects instantiated from the class.

8. The computer program product of claim 5, wherein:

the chemical experiment has an experiment type corresponding to one of a set of one or more experiment types;

the chemical experiment is represented by a generic experiment object and a derived experiment object, the generic experiment object having a classname property and a library ID property, the classname property associated with the experiment type of the chemical experiment and the library ID property identifying the library of materials, the derived experiment object having a plurality of derived experiment class properties derived from the associated experiment type; and the instructions operable to cause a programmable processor to parse the representation include instructions operable to cause a programmable processor to map the generic experiment object to a database table including data for experiments having a plurality of different experiment types in the set of experiment types and map the derived experiment object to a database table including data only for experiments having the experiment type of the chemical experiment.

9. A computer-implemented laboratory data management system for processing data from a chemical experiment involving a library of materials, the system comprising:

one or more client processes running on one or more computers coupled to a network, at least one of the client processes being operable to receive data from a chemical experiment on a library of materials having a plurality of members and associate the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials; and a database server process running on a computer coupled to the network, the database server process being operable to receive the representation of the chemical experiment and to parse the representation to map the data from the chemical experiment to tables in a relational database stored in a memory coupled to the network based on the experiment object properties.

10. A computer-implemented method for processing data from a chemical experiment on a library of materials, the method comprising:

receiving data from a chemical experiment on a library of materials having a plurality of members;

associating the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials; and parsing the representation to map a subset of the data from the representation to tables in a relational database based on the properties of the experiment object.

11. The method of claim 10, wherein:

parsing the representation includes mapping a first subset of the data from the representation to a first set of database tables based on a first mapping schema and a second subset of the data from the chemical experiment to a second set of database tables based on a second mapping schema, the first mapping schema being different from the second mapping schema.

12. The method of claim 11, wherein:

the first subset of the data is different from the second subset of the data.

13. A computer-implemented method for processing data from a chemical experiment on a library of materials, the method comprising:

receiving data from a chemical experiment on a library of materials having a plurality of members;

associating the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials; and parsing the representation to map data from the representation to a first set of database tables based on a first mapping schema and a second set of database tables based on a second mapping schema, the first set of database tables being different from the second set of database tables.

14. A computer program product on a computer-readable medium for processing data from a chemical experiment on a library of materials, the computer program product comprising instructions operable to cause a programmable processor to:

receive data from a chemical experiment on a library of materials having a plurality of members;

associate the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials; and parse the representation to map a subset of the data from the representation to tables in a relational database based on the properties of the experiment object.

15. The computer program product of claim 14, wherein: the instructions operable to cause a programmable processor to parse the representation include instructions operable to cause a programmable processor to map a first subset of the data from the representation to a first set of database tables based on a first mapping schema and a second subset of the data from the chemical experiment to a second set of database tables based on a second mapping schema, the first mapping schema being different from the second mapping schema.

16. The computer program product of claim 15, wherein: the first subset of the data is different from the second subset of the data.

17. A computer program product on a computer-readable medium for processing data from a chemical experiment on a library of materials, the computer program product comprising instructions operable to cause a programmable processor to:

receive data from a chemical experiment on a library of materials having a plurality of members;

associate the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials; and parse the representation to map data from the representation to a first set of database tables based on a first mapping schema and a second set of database tables based on a second mapping schema, the first set of database tables being different from the second set of database tables.

18. A computer-implemented laboratory data management system for processing data from a chemical experiment involving a library of materials, the system comprising:

one or more client processes running on one or more computers coupled to a network, at least one of the client processes being operable to receive data from a chemical experiment on a library of materials having a plurality of members and associate the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials; and a database server process running on a computer coupled to the network, the database server process being operable to receive the representation of the chemical experiment and to parse the representation to map a subset of the data from the representation to tables in a relational database based on the experiment object properties.

19. The laboratory data management system of claim 18, wherein:

the database server process is operable to map a first subset of the data from the representation to a first set of database tables based on a first mapping schema and a second subset of the data from the chemical experiment to a second set of database tables based on a second mapping schema, the first mapping schema being different from the second mapping schema.

20. The laboratory data management system of claim 19, wherein:

the first subset of the data is different from the second subset of the data.

21. A computer-implemented laboratory data management system for processing data from a chemical experiment involving a library of materials, the system comprising:

one or more client processes running on one or more computers coupled to a network, at least one of the client processes being operable to receive data from a chemical experiment on a library of materials having a plurality of members and associate the received data with a representation of the chemical experiment, the representation including data defining an experiment object having a plurality of properties derived from the chemical experiment, the experiment object being associated with the library of materials, the representation also including data defining one or more element objects, each element object being associated with one or more members of the library of materials; and a database server process running on a computer coupled to the network, the database server process being operable to receive the representation of the chemical experiment and to parse the representation to map the data from the representation to a first set of database tables based on a first mapping schema and a second set of database tables based on a second mapping schema, the first set of database tables being different from the second set of database tables.

22. A laboratory data management system for processing data from chemical experiment involving a library of materials, the system comprising:

one or more client processes running on one or more computers coupled to a network, each client process being operable to generate a data set including a value for each of a plurality of members of a library of materials and to generate an intermediate representation of the data set, the intermediate representation including data defining an experiment object having a plurality of properties derived from the chemical experiment, the plurality of properties including a data set object assigning each first data set value to one of a set of elements corresponding to a plurality of members of the library of materials;

a middle-tier server process running on a computer coupled to the network, the middle-tier server process being operable to receive the intermediate representation and to parse the intermediate representation to map the element values to database tables according to a predetermined database schema, wherein the middle-tier server process is operable to map the element values from the intermediate representation to a first set of database tables according to a first predetermined database schema and a second set of database tables according to a second predetermined database schema, the first set of database tables being different from the second set of database tables; and a database process running on a computer coupled to the network, the database process being operable to store the element values in a memory coupled to the network.

23. A computer-implemented method for processing data from experiments performed on libraries of materials, comprising:

receiving data from a chemical experiment on a library of materials having a plurality of members, the chemical experiment having an experiment type from a set of experiment types; and associating the received data with a representation of the chemical experiment, the representation including data defining a first experiment object and a second experiment object, the first experiment object being associated with the library of materials, the second experiment object having a plurality of properties derived from the experiment type of the chemical experiment and being associated with one or more element objects representing members of the library of materials, each of the one or more element objects being associated in the representation with data from the received data for the corresponding library member.

24. The method of claim 23, further comprising:

providing an experiment base class and one or more derived experiment classes, the experiment base class having a set of class properties including a library ID property for identifying a library of materials and a derived experiment class property for identifying an experiment type from the set of experiment types, each derived experiment class being associated with one of a set of experiment types and having a plurality of derived experiment class properties derived from the associated experiment type; and generating the representation of the chemical experiment, the first experiment object being instantiated from the experiment base class, the first experiment object having a library ID value identifying the library of materials and a derived experiment class value identifying the experiment type of the chemical experiment, the second experiment object being instantiated from the derived experiment class corresponding to the experiment type of the chemical experiment and including the one or more element objects representing members of the library of materials.

25. The method of claim 23, wherein:

the second experiment object references the one or more element objects representing the library of materials as children in an object hierarchy.

26. The method of claim 23, further comprising:

generating a representation of a second chemical experiment performed on the library of materials, the representation of the second chemical experiment including one or more additional experiment objects associated with the library of materials.

27. The method of claim 23, further comprising:

parsing the representation to map the received data to one or more tables in a relational database; and storing the received data in the relational database according to the mapping.

28. A computer program product on a computer-readable medium for processing data from a chemical experiment on a library of materials, the computer program product comprising instructions operable to cause a programmable processor to:

receive data from a chemical experiment on a library of materials having a plurality of members, the chemical experiment having an experiment type from a set of experiment types; and associate the received data with a representation of the chemical experiment, the representation including data defining a first experiment object and a second experiment object, the first experiment object being associated with the library of materials, the second experiment object having a plurality of properties derived from the experiment type of the chemical experiment and being associated with one or more element objects representing members of the library of materials, each of the one or more element objects being associated in the representation with data from the received data for the corresponding library member.

29. The computer program product of claim 28, further comprising instructions operable to cause a programmable processor to:

provide an experiment base class and one or more derived experiment classes, the experiment base class having a set of class properties including a library ID property for identifying a library of materials and a derived experiment class property for identifying an experiment type from the set of experiment types, each derived experiment class being associated with one of a set of predetermined experiment types and having a plurality of derived experiment class properties derived from the associated experiment type; and generate the representation of the chemical experiment, the first experiment object being instantiated from the experiment base class, the first experiment object having a library ID value identifying the library of materials and a derived experiment class value identifying the experiment type of the chemical experiment, the second experiment object being instantiated from the derived experiment class corresponding to the experiment type of the chemical experiment and including the one or more element objects representing members of the library of materials.

30. The computer program product of claim 28, wherein:

the second experiment object references the one or more element objects representing the library of materials as children in an object hierarchy.

31. The computer program product of claim 28, further comprising instructions operable to cause a programmable processor to:

generate a representation of a second chemical experiment performed on the library of materials, the representation of the second chemical experiment including one or more additional experiment objects associated with the library of materials.

32. The computer program product of claim 28, further comprising instructions operable to cause a programmable processor to:

parse the representation to map the received data to one or more tables in a relational database; and store the received data in the relational database according to the mapping.

* * * * *

UNITED STATES PATENT AND TRADEMARK OFFICE
CERTIFICATE OF CORRECTION

PATENT NO. : 7,085,773 B2
APPLICATION NO. : 10/250618
DATED : August 1, 2006
INVENTOR(S) : Dorsett, Jr.

It is certified that error appears in the above-identified patent and that said Letters Patent is hereby corrected as shown below:

On the coversheet of the patent, [56] Foreign Patent Documents, add:

--WO 00/23921 4/2000--

On page 2, [56] Other Publications, Column 1, please change the Afferent Systems, Inc. reference to read:
--Afferent Systems, Inc., "Afferent Analytical™", pp. 1 of 1, http://www.afferent.com/analytical.html, Copyright© 1996-1999, Last updated Jan. 28, 1999.--

On page 2, [56] Other Publications, Column 2, please change the Keller, et al. reference to read:
--Keller et al., "Metadata: The Foundation of Effective Experiment Management", Proc. Of the 1$^{st}$ IEEE Meta-
data Conference, Silver Springs, Maryland, USA, 1996 (12 pages).--

--On page 3, [56] Other Publications, Column 1, please change the Microsoft Building A Custom Project Wizard in Visual Studio.NET reference to read:
Microsoft Building A Custom Project Wizard in Visual Studio.NET, May 2003, downloaded on Aug. 18, 2004 from: http://msdn.microsof.com/library/en-us/dv_vstechart/html/customprojectwiz.asp?frame=true--

On page 3, [56] Other Publications, Column 1, please change the Microsoft Creating Components in .NET reference to read:
--Microsoft Creating Components in .NET , Feb. 2002, down-loaded on Aug. 18, 2004 from: http://msdn.microsof.com/library/en-us/dpdotnet/html/componentsnet.asp?frame=true.--

On page 3, [56] Other Publications, Column 1, please change the Microsoft Writing Custom Designers for .NET Components reference to read:
--Microsoft Writing Custom Designers for .NET Components, Jun. 2001, downloaded on Aug. 18, 2004 from: http://msdn.microsof.com/library/en-us/dndotnet//html/custdsgnr-dotnet.asp?frame=true.--

UNITED STATES PATENT AND TRADEMARK OFFICE
CERTIFICATE OF CORRECTION

PATENT NO.        : 7,085,773 B2
APPLICATION NO. : 10/250618
DATED             : August 1, 2006
INVENTOR(S)       : Dorsett, Jr.

It is certified that error appears in the above-identified patent and that said Letters Patent is hereby corrected as shown below:

Col. 48, line 46, insert --a-- between "from" and "chemical"

Signed and Sealed this

Twenty-seventh Day of March, 2007

JON W. DUDAS
*Director of the United States Patent and Trademark Office*